United States Patent
Auld

(10) Patent No.: US 9,931,170 B2
(45) Date of Patent: Apr. 3, 2018

(54) METHODS, SYSTEMS, AND DEVICES FOR MOVING A SURGICAL INSTRUMENT COUPLED TO A ROBOTIC SURGICAL SYSTEM

(71) Applicant: Ethicon Endo-Surgery, LLC, Guaynabo, PR (US)

(72) Inventor: Michael D. Auld, Cincinnati, OH (US)

(73) Assignee: Ethicon Endo-Surgery, LLC, Guaynabo, PR (US)

( * ) Notice: Subject to any disclaimer, the term of this patent is extended or adjusted under 35 U.S.C. 154(b) by 122 days.

(21) Appl. No.: 14/989,057

(22) Filed: Jan. 6, 2016

(65) Prior Publication Data

US 2017/0189128 A1    Jul. 6, 2017

(51) Int. Cl.
*B25J 9/18* (2006.01)
*A61B 34/30* (2016.01)
*A61B 34/37* (2016.01)

(52) U.S. Cl.
CPC .............. *A61B 34/30* (2016.02); *A61B 34/37* (2016.02); *A61B 2034/305* (2016.02)

(58) Field of Classification Search
CPC .. H02P 6/16; H02P 7/06; B25J 9/1689; G05B 2219/45117
See application file for complete search history.

(56) References Cited

U.S. PATENT DOCUMENTS

| 8,831,782 | B2 | 9/2014 | Itkowitz |
| 2009/0202387 | A1 | 8/2009 | Dlugos, Jr. et al. |
| 2012/0158013 | A1 | 6/2012 | Stefanchik et al. |
| 2013/0282021 | A1* | 10/2013 | Parihar ............... A61B 17/105 |
| | | | 606/130 |

FOREIGN PATENT DOCUMENTS

| WO | WO-2014151621 A1 | 9/2014 |
| WO | WO-2014151952 A1 | 9/2014 |

\* cited by examiner

*Primary Examiner* — Karen Masih
(74) *Attorney, Agent, or Firm* — Mintz Levin Cohn Ferris Glovsky and Popeo, P.C.

(57) ABSTRACT

Various exemplary methods, systems, and devices for moving a surgical instrument coupled to a robotic surgical system are provided. In general, a robotic surgical system can include a movement assembly configured to facilitate movement of surgical instrument coupled to the robotic surgical system, e.g., coupled to an electromechanical arm of the robotic surgical system. The movement can include translational movement of the surgical instrument in which the instrument is selectively advanceable and retractable in opposed directions, e.g., proximal direction and distal direction, up vertically and down vertically, etc. The translational movement can be along a shaft of the instrument such that the movement assembly can be configured to selectively translate the instrument along a longitudinal axis of the shaft.

19 Claims, 14 Drawing Sheets

METHODS, SYSTEMS, AND DEVICES FOR MOVING A SURGICAL INSTRUMENT COUPLED TO A ROBOTIC SURGICAL SYSTEM

FIELD OF THE INVENTION

The present invention relates to methods, systems, and devices for moving a surgical instrument coupled to a robotic surgical system.

BACKGROUND OF THE INVENTION

Minimally invasive surgical (MIS) instruments are often preferred over traditional open surgical devices due to the reduced post-operative recovery time and minimal scarring. Laparoscopic surgery is one type of MIS procedure in which one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. The instruments and tools can be used to engage and/or treat tissue in a number of ways to achieve a diagnostic or therapeutic effect. Endoscopic surgery is another type of MIS procedure in which elongate flexible shafts are introduced into the body through a natural orifice.

Various robotic systems have been developed to assist in MIS procedures. Robotic systems can allow for more intuitive hand movements by maintaining both natural eye-hand axis. Robotic systems can also allow for more degrees of freedom in movement by including a "wrist" joint on the instrument, creating a more natural hand-like articulation. One drawback with robotic systems, however, is that it can be difficult for the robotic systems to securely grasp, and therefore accurately move, instruments of different sizes. Since different instruments have different sizes, e.g., different shaft diameters, the robotic system may not be able to be used with certain instruments due to their size being too large or too small to be grasped by the robotic system and/or the robotic system may not be able to securely grasp some instruments as well as other instruments and thus be unable to move some instruments as accurately as other instruments. Even small instrument movement errors can cause any number of adverse effects during surgery, such as interference with other instruments, visual obstruction of other instruments and/or patient anatomy, and/or patient injury.

Accordingly, there remains a need for improved methods, systems, and devices for moving a surgical instrument coupled to a robotic surgical system.

SUMMARY OF THE INVENTION

In general, methods, systems, and devices for moving a surgical instrument coupled to a robotic surgical system are provided.

In one aspect, a surgical system is provided that in one embodiment includes an electromechanical arm configured for movement in multiple axes, an electromechanical tool having an instrument shaft and an end effector formed thereon, and a tool controller operatively coupled to the electromechanical arm and the electromechanical tool. The electromechanical tool is configured to be mounted on the electromechanical arm, and the electromechanical tool is configured to move relative to the electromechanical arm. The tool controller includes opposed rollers that receive the electromechanical tool therebetween. The rollers are configured for cooperative rotational movement effective to translate the electromechanical tool. The rollers are configured for linear movement toward and away from the electromechanical tool and thereby accommodate a diameter of the electromechanical tool while providing a compressive force on the electromechanical tool.

The surgical system can vary in any number of ways. For example, the tool controller can include opposed worm gears that are each operatively coupled to one of the opposed rollers. The worm gears can be configured for cooperative rotational movement effective to cause the rotational movement of the rollers.

For another example, the tool controller can include a single worm gear operatively coupled to one of the opposed rollers and configured to rotate to cause rotation of both of the opposed rollers.

For yet another example, the tool controller can include opposed gears each having one of the rollers operatively coupled thereto. The gears can be configured for cooperative rotational movement effective to cause the rotational movement of the rollers. The tool controller can include opposed worm gears that each have teeth, and each of the opposed gears has teeth operatively engaged with the teeth of one of the worm gears. The worm gears can be configured for cooperative rotational movement effective to cause the rotational movement of the opposed gears.

For still another example, the compressive force can be a variable force dependent on the diameter of the electromechanical tool.

For another example, the surgical system can include a second electromechanical tool having a second instrument shaft and a second end effector formed thereon. The second electromechanical tool can be configured to be mounted on the electromechanical arm, the second electromechanical tool can be configured to move relative to the electromechanical arm, a diameter of the second electromechanical tool can be different than the diameter of the electromechanical tool, the rollers can be configured for linear movement toward and away from the second electromechanical tool and thereby accommodate the diameter of the second electromechanical tool while providing a second compressive force on the second electromechanical tool, and the second compressive force can be different than the compressive force.

For another example, the surgical system can include a processor configured to receive a user input and configured to cause the cooperative rotational movement of the rollers in response to the received user input.

In another embodiment, a surgical system is provided that includes an electromechanical arm configured to removably couple to a surgical instrument, and a worm drive operatively coupled to the electromechanical arm. The electromechanical arm is configured to move so as to move the surgical instrument removably coupled thereto relative to a patient on which a surgical procedure is being performed. The worm drives can be configured to grip a shaft of the surgical instrument, and the worm drive can be configured to move and thereby cause longitudinal translation of the shaft of the surgical instrument removably coupled to the electromechanical arm.

The surgical system can have any number of variations. For example, the worm drive can include a first wheel and a first worm gear operatively engaged with the first wheel, and can include a second wheel and a second worm gear operatively engaged with the second wheel. In at least some embodiments, the first and second wheels can be configured to simultaneously rotate in opposite directions and thereby cause the longitudinal translation of the surgical instrument removably coupled to the electromechanical arm, and the first and second worm gears can each be configured to simultaneously rotate to cause the first and second wheels to simultaneously rotate in the opposite directions. In at least some embodiments, each of the first and second wheels can include a gear and a roller. The gear of the first wheel can be operatively engaged with the first worm gear, the gear of the second wheel can be operatively engaged with the second worm gear, and the roller of the first wheel and the roller of the second wheel can be configured to simultaneously grip the shaft of the surgical instrument. Each of the rollers can be configured to move in a direction perpendicular to a direction of the longitudinal translation of the shaft of the surgical instrument. In at least some embodiments, each of the rollers can be configured to move in a direction perpendicular to a direction of the longitudinal translation of the shaft of the surgical instrument.

For another example, the worm drive can include a first wheel, a second wheel operatively engaged with the first wheel, and a first worm gear operatively engaged with the first wheel. In at least some embodiments, each of the rollers can be configured to move in a direction perpendicular to a direction of the longitudinal translation of the shaft of the surgical instrument.

For still another example, the worm drive can be configured to rotate and thereby cause the longitudinal translation of the shaft of the surgical instrument. For yet another example, the worm drive can be configured to move linearly and thereby accommodate grasping of shafts having different diameters. For still another example, the surgical system can include a surgical instrument having a shaft configured to be gripped by the worm drive. For another example, the surgical system can include a user input device configured to receive an input from a user indicative of a desired movement of the surgical instrument removably coupled to the electromechanical arm, and a processor configured to receive the input from the user input device. The processor can be configured to cause the worm drive to move in response to the received input.

In yet another embodiment, a surgical system is provided that includes an electromechanical arm configured for movement in multiple axes, a pliable sleeve coupled to the electromechanical arm, an electromechanical tool having an instrument shaft and an end effector formed thereon, and a tool driver having opposed rotors having the pliable sleeve positioned therebetween. The electromechanical tool is configured to be mounted within the pliable sleeve. The opposed rotors each have a plurality of lobes and are each capable of cooperative rotational movement such that the lobes sequentially engage the pliable sleeve to generate sufficient friction to translate the electromechanical tool within the pliable sleeve.

The surgical system can vary in any number of ways. For example, the opposed rotors can each include a central base having the plurality of lobes extending radially outward therefrom. For another example, the opposed rotors can each include a belt having the plurality of lobes and a roller configured to rotate to drive the belt. For yet another example, the translation of the electromechanical tool within the pliable sleeve can include longitudinal translation of the electromechanical tool along a longitudinal axis of the instrument shaft of the electromechanical tool. For still another example, the surgical system can include a processor configured to receive a user input and configured to cause the cooperative rotational movement of the lobes in response to the received user input.

In another embodiment, a surgical system is provided that includes an electromechanical arm configured to removably couple to a surgical instrument, an elastomeric sleeve configured to receive the surgical instrument therein, and a peristaltic pump operatively coupled to the electromechanical arm. The electromechanical arm is configured to move so as to move the surgical instrument removably coupled thereto relative to a patient on which a surgical procedure is being performed. The peristaltic pump includes opposed rotors each configured to rotate to apply a cooperative force to the sleeve and thereby cause the surgical instrument received in the sleeve to longitudinally translate relative to the sleeve.

The surgical system can have any number of variations. For example, the opposed rotors can each include a central base having a plurality of lobes extending radially outward therefrom. For another example, the opposed rotors can each include a belt having a plurality of lobes and a roller configured to rotate to drive the belt. For yet another example, the surgical system can include a processor configured to receive a user input and configured to cause the rotation of the opposed rotors in response to the received user input.

In another aspect, a method for performing surgery is provided that in one embodiment includes positioning an electromechanical tool having an instrument shaft between a first worm wheel and a second worm wheel. A first surface of the instrument shaft is proximate to the first worm wheel and a second surface of the instrument shaft is proximate to the second worm wheel. The method also includes activating a worm shaft to rotate in a first direction and produce a first worm wheel torque. The activation of the worm shaft is controlled by a controller. The method also includes manipulating a first parallel reaction force in the first worm wheel and a second parallel reaction force in the second worm wheel to produce a lateral force, and simultaneously manipulating the lateral force between the first worm wheel and the first surface and the second worm wheel and the second surface to increase an interface pressure on the first and second surfaces. The method can vary in any number of ways.

In another embodiment, a method for performing surgery is provided that includes positioning a surgical tool having an instrument shaft within an elastomeric sleeve coupled between a peristaltic pump having a twin rotor configuration. A first surface of the instrument shaft is proximate to the first rotor and a second surface of the instrument shaft is proximate to the second rotor. The method also includes activating the peristaltic pump to rotate the first rotor in a first direction and the second rotor in a second direction, thereby creating a friction force between the rotors and the elastomeric sleeve and the instrument shaft. The method also includes manipulating the friction force to produce a lateral force to laterally translate the instrument shaft of the surgical tool. The method can have any number of variations.

Non-transitory computer program products (i.e., physically embodied computer program products) are also provided that store instructions, which when executed by one or more processors of one or more computer systems, causes at least one processor to perform operations herein. Similarly, computer systems are also provided that can include one or more processors and one or more memories coupled to the one or more processors. Each of the one or more memories can temporarily or permanently store instructions that cause at least one processor to perform one or more of the operations described herein. In addition, methods can be implemented by one or more processors either within a single computer system or distributed among two or more computer systems. Such computer systems can be connected and can exchange data and/or commands or other instructions or the like via one or more connections, including but not limited to a connection over a network (e.g., the Internet, a wireless wide area network, a local area network, a wide area network, a wired network, etc.), via a direct connection between one or more of the multiple computer systems, etc.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
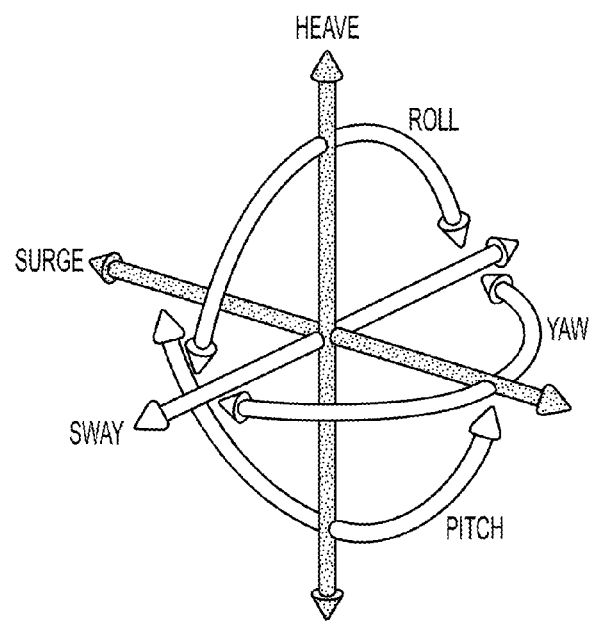
FIG. 1 is a graphical representation of terminology associated with six degrees of freedom.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

It will be appreciated that the terms "proximal" and "distal" are used herein with reference to a user, such as a clinician, gripping a handle of an instrument. Other spatial terms such as "front" and "back" similarly correspond respectively to distal and proximal. It will be further appreciated that for convenience and clarity, spatial terms such as "vertical" and "horizontal" are used herein with respect to the drawings. However, surgical instruments are used in many orientations and positions, and these spatial terms are not intended to be limiting and absolute.

Various exemplary methods, systems, and devices for moving a surgical instrument coupled to a robotic surgical system are provided. In general, a robotic surgical system can include a movement assembly configured to facilitate movement of surgical instrument coupled to the robotic surgical system, e.g., coupled to an electromechanical arm of the robotic surgical system. The movement can include translational movement of the surgical instrument in which the instrument is selectively advanceable and retractable in opposed directions, e.g., proximal direction and distal direction, up vertically and down vertically, etc. The translational movement can be along a shaft of the instrument such that the movement assembly can be configured to selectively translate the instrument along a longitudinal axis of the shaft. Surgical instruments coupled to robotic surgical systems are often single shafted, e.g., have only one shaft with an end effector at a distal end thereof. Moving a surgical instrument along a longitudinal axis of the instrument's shaft can thus selectively move the end effector toward and away from an intended target, e.g., an organ, a blood vessel, another surgical instrument, etc., which may facilitate use of the end effector in its specific surgical function, e.g., grasping, needle driving, cutting, electrocauterizing, stapling, clip applying, clip removing, suctioning, irrigating, retracting, etc.

Surgical instruments are available with many different standard diameters, e.g., 3 mm, 5 mm, 15 mm, 10 mm, etc. The movement assembly can be configured to accommodate surgical instrument shafts having any of a plurality of different diameters, which may allow the robotic surgical system to be compatible with many different surgical instruments and/or may allow the robotic surgical system to be compatible with shafts having non-standard size diameters. The robotic surgical system may thus not be limited to use with only one size of surgical instrument or limited to use with a limited number of predetermined sizes of surgical instruments. The movement assembly can be configured to automatically adjust to the diameter of the shaft of the surgical instrument coupled to the robotic surgical system such that a user need not spend time adjusting robotic surgical system to accommodate a specific shaft diameter size or learning how to make such an adjustment.

The movement assembly can be configured to securely grasp the surgical instrument when the instrument is not moving (e.g., when the instrument is stationary) as well as when the instrument is moving (e.g., when the instrument is slidably translating), which may prevent unintended slippage of the instrument. Unintended slippage can cause any one or more problems, such as patient injury, damage to the instrument, damage to the robotic surgical system, and interference with other surgical instrument(s).

Shafts of surgical instruments are often smooth to facilitate formation of a seal around the instrument in a trocar or other access device. The smoothness can encourage unintended slippage. The movement assembly being configured to securely grasp a shaft of a surgical instrument may help prevent unintended slippage of the shaft, even when the shaft is smooth.

At least some of the methods, systems, and devices for moving a surgical instrument coupled to a robotic surgical system provided herein can include a movement assembly configured to provide a lateral force to a surgical instrument, e.g., to a shaft of the instrument, coupled to the robotic surgical system. The lateral force can be relative to a longitudinal axis of the instrument's shaft so as to provide a pinching force on the shaft. The lateral force may facilitate secure gripping of the instrument by the robotic surgical system, e.g., by the movement assembly thereof, and thus help prevent unintended slippage of the instrument while the instrument is coupled to the robotic surgical system regardless of whether the instrument shaft is moving or is stationary. A movement assembly configured to provide a lateral force to a surgical instrument can have a variety of configurations. For example, as discussed further below, the movement assembly can include a pair of opposed rollers configured to grasp the instrument, e.g., a shaft of the instrument, therebetween.

At least some of the methods, systems, and devices for moving a surgical instrument coupled to a robotic surgical system provided herein can include a movement assembly configured to peristaltically drive a surgical instrument coupled to the robotic surgical system to cause translational movement of the instrument. A movement assembly configured to peristaltically drive a surgical instrument can have a variety of configurations. For example, as discussed further below, the movement assembly can include a tubular sleeve configured to receive the instrument therein (e.g., a shaft of the instrument therein) and a pair of opposed rotors configured to apply a pumping action to the sleeve and thereby cause translational movement of the instrument within the sleeve. The sleeve may help protect sterility of the instrument received therein, may help trap fluid and other debris therein between an inner surface of the sleeve and an outer surface of the instrument received in the sleeve and thereby help prevent the fluid and debris from getting stuck in or otherwise interfering with other parts of the robotic surgical system, and/or may be disposable after use and thereby facilitate cleaning of the robotic surgical system for re-use.

Each of a movement assembly configured to provide a lateral force to a surgical instrument coupled to the robotic surgical system and a movement assembly configured to peristaltically drive a surgical instrument coupled to the robotic surgical system can be configured to translate rotational movement thereof (e.g., rotation of rollers, rotation of pump rotors, etc.) into translational movement (e.g., linear, non-rotational movement) of the instrument.

TERMINOLOGY

There are a number of ways in which to describe the movement of a surgical system, as well as its position and orientation in space. One particularly convenient convention is to characterize a system in terms of its degrees of freedom. The degrees of freedom of a system are the number of independent variables that uniquely identify its pose or configuration. The set of Cartesian degrees of freedom is usually represented by the three translational or position variables, e.g., surge, heave, sway, and by the three rotational or orientation variables, e.g., Euler angles or roll, pitch, yaw, that describe the position and orientation of a component of a surgical system with respect to a given reference Cartesian frame. As used herein, and as illustrated in FIG. 1, the term "surge" refers to forward and backward movement, the term "heave" refers to movement up and down, and the term "sway" refers to movement left and right. With regard to the rotational terms, "roll" refers to tilting side to side, "pitch" refers to tilting forward and backward, and "yaw" refers to turning left and right. In a more general sense, each of the translation terms refers to movement along one of the three axes in a Cartesian frame, and each of the rotational terms refers to rotation about one of the three axes in a Cartesian frame.

Although the number of degrees of freedom is at most six, a condition in which all the translational and orientational variables are independently controlled, the number of joint degrees of freedom is generally the result of design choices that involve considerations of the complexity of the mechanism and the task specifications. For non-redundant kinematic chains, the number of independently controlled joints is equal to the degree of mobility for an end effector. For redundant kinematic chains, the end effector will have an equal number of degrees of freedom in Cartesian space that will correspond to a combination of translational and rotational motions. Accordingly, the number of degrees of freedom can be more than, equal to, or less than six.

With regard to characterizing the position of various components of the surgical system and the mechanical frame, the terms "forward" and "rearward" may be used. In general, the term "forward" refers to an end of the surgical system that is closest to the distal end of the input tool, and when in use in a surgical procedure, to the end disposed within a patient's body. The term "rearward" refers to an end of the surgical system farthest from the distal end of the input tool, and when in use, generally to the end farther from the patient.

The terminology used herein is not intended to limit the invention. For example, spatially relative terms, e.g., "superior," "inferior," "beneath," "below," "lower," "above," "upper," "rearward," "forward," etc., may be used to describe one element's or feature's relationship to another element or feature as illustrated in the figures. These spatially relative terms are intended to encompass different positions and orientations of the device in use or operation in addition to the position and orientation shown in the figures. For example, if the device in the figures is turned over, elements described as "inferior to" or "below" other elements or features would then be "superior to" or "above" the other elements or features. Likewise, descriptions of movement along and around various axes includes various special device positions and orientations. As will be appreciated by those skilled in the art, specification of the presence of stated features, steps, operations, elements, and/or components does not preclude the presence or addition of one or more other features, steps, operations, elements, components, and/or groups described herein. In addition, components described as coupled may be directly coupled, or they may be indirectly coupled via one or more intermediate components.

There are several general aspects that apply to the various descriptions below. For example, at least one surgical end effector is shown and described in various figures. An end effector is the part of a minimally invasive or invasive surgical instrument or assembly that performs a specific surgical function, e.g., forceps/graspers, needle drivers, scissors, electrocautery hooks, staplers, clip appliers/removers, suction tools, irrigation tools, etc. Any end effector can be utilized with the surgical system described herein. Further, in exemplary embodiments, an end effector can be configured to be manipulated by a user input tool. The input tool can be any tool that allows successful manipulation of the end effector, whether it be a tool similar in shape and style to the end effector, such as an input tool of scissors similar to end effector scissors, or a tool that is different in shape and style to the end effector, such as an input tool of a glove dissimilar to end effector graspers, and such as input tool of a joystick dissimilar to end effector graspers. In at least some embodiments, the input tool can be a larger scaled version of the end effector to facilitate ease of use. Such a larger scale input tool can have finger loops or grips of a size suitable for a user to hold. However, the end effector and the input tool can have any relative size.

A slave tool, e.g., a surgical instrument, of the surgical system can be positioned inside a patient's body cavity through an access point in a tissue surface for minimally invasive surgical procedures. Typically, cannulas such as trocars are used to provide a pathway through a tissue surface and/or to prevent a surgical instrument or guide tube from rubbing on patient tissue. Cannulas can be used for both incisions and natural orifices. Some surgical procedures require insufflation, and the cannula can include one or more seals to prevent excess insufflation gas leakage past the instrument or guide tube. In at least some embodiments, the cannula can have a housing coupled thereto with two or more sealed ports for receiving various types of instruments besides the slave assembly. As will be appreciated by a person skilled in the art, any of the surgical system components disclosed herein can have a functional seal disposed thereon, therein, and/or therearound to prevent and/or reduce insufflation leakage while any portion of the surgical system is disposed through a surgical access port, such as a cannula. The surgical system can also be used in open surgical procedures. As used herein, a surgical access point is a point at which the slave tool enters a body cavity through a tissue surface, whether through a cannula in a minimally invasive procedure or through an incision in an open procedure.

Computer Systems

The systems, devices, and methods disclosed herein can be implemented using one or more computer systems, which may also be referred to herein as digital data processing systems and programmable systems.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computer system may include clients and servers. A client and server are generally remote from each other and typically interact through a communication network. The relationship of client and server arises by virtue of computer programs running on the respective computers and having a client-server relationship to each other.

The computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, e.g., a mouse, a trackball, etc., by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

Figure 2:
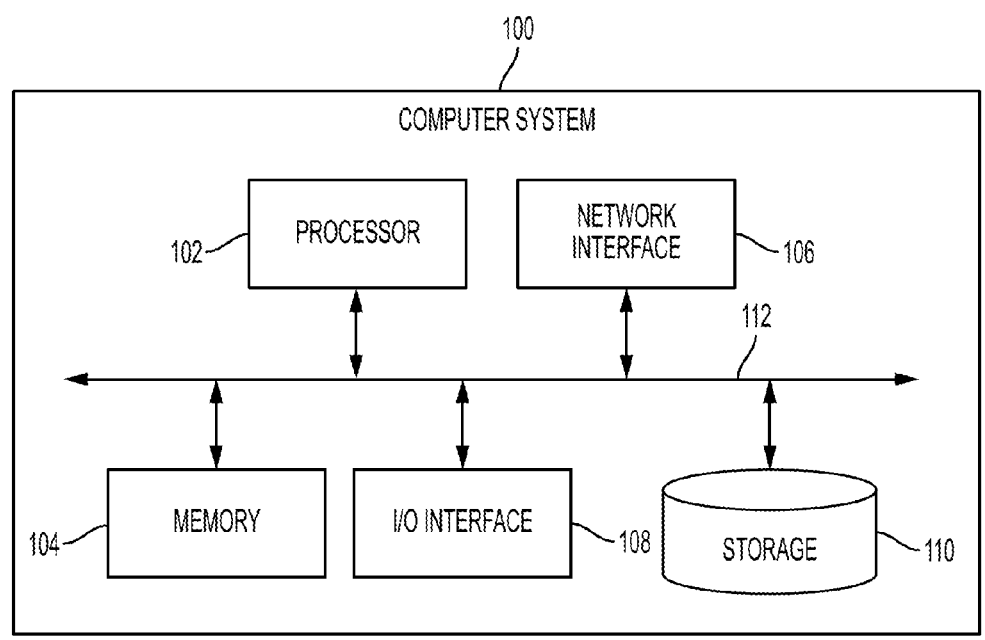
FIG. 2 is a schematic view of one embodiment of a computer system.

FIG. 2 illustrates one exemplary embodiment of a computer system 100. As shown, the computer system 100 can include one or more processors 102 which can control the operation of the computer system 100. "Processors" are also referred to herein as "controllers." The processor(s) 102 can include any type of microprocessor or central processing unit (CPU), including programmable general-purpose or special-purpose microprocessors and/or any one of a variety of proprietary or commercially available single or multi-processor systems. The computer system 100 can also include one or more memories 104, which can provide temporary storage for code to be executed by the processor(s) 102 or for data acquired from one or more users, storage devices, and/or databases. The memory 104 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system 100 can be coupled to a bus system 112. The illustrated bus system 112 is an abstraction that represents any one or more separate physical busses, communication lines/interfaces, and/or multi-drop or point-to-point connections, connected by appropriate bridges, adapters, and/or controllers. The computer system 100 can also include one or more network interface(s) 106, one or more input/output (IO) interface(s) 108, and one or more storage device(s) 110.

The network interface(s) 106 can enable the computer system 100 to communicate with remote devices, e.g., other computer systems, over a network, and can be, for non-limiting example, remote desktop connection interfaces, Ethernet adapters, and/or other local area network (LAN) adapters. The IO interface(s) 108 can include one or more interface components to connect the computer system 100 with other electronic equipment. For non-limiting example, the IO interface(s) 108 can include high speed data ports, such as universal serial bus (USB) ports, 1394 ports, Wi-Fi, Bluetooth, etc. Additionally, the computer system 100 can be accessible to a human user, and thus the IO interface(s) 108 can include displays, speakers, keyboards, pointing devices, and/or various other video, audio, or alphanumeric interfaces. The storage device(s) 110 can include any conventional medium for storing data in a non-volatile and/or non-transient manner. The storage device(s) 110 can thus hold data and/or instructions in a persistent state, i.e., the value is retained despite interruption of power to the computer system 100. The storage device(s) 110 can include one or more hard disk drives, flash drives, USB drives, optical drives, various media cards, diskettes, compact discs, and/or any combination thereof and can be directly connected to the computer system 100 or remotely connected thereto, such as over a network. In an exemplary embodiment, the storage device(s) can include a tangible or non-transitory computer readable medium configured to store data, e.g., a hard disk drive, a flash drive, a USB drive, an optical drive, a media card, a diskette, a compact disc, etc.

The elements illustrated in FIG. 2 can be some or all of the elements of a single physical machine. In addition, not all of the illustrated elements need to be located on or in the same physical machine. Exemplary computer systems include conventional desktop computers, workstations, minicomputers, laptop computers, tablet computers, personal digital assistants (PDAs), mobile phones, and the like.

The computer system 100 can include a web browser for retrieving web pages or other markup language streams, presenting those pages and/or streams (visually, aurally, or otherwise), executing scripts, controls and other code on those pages/streams, accepting user input with respect to those pages/streams (e.g., for purposes of completing input fields), issuing HyperText Transfer Protocol (HTTP) requests with respect to those pages/streams or otherwise (e.g., for submitting to a server information from the completed input fields), and so forth. The web pages or other markup language can be in HyperText Markup Language (HTML) or other conventional forms, including embedded Extensible Markup Language (XML), scripts, controls, and so forth. The computer system 100 can also include a web server for generating and/or delivering the web pages to client computer systems.

In an exemplary embodiment, the computer system 100 can be provided as a single unit, e.g., as a single server, as a single tower, contained within a single housing, etc. The single unit can be modular such that various aspects thereof can be swapped in and out as needed for, e.g., upgrade, replacement, maintenance, etc., without interrupting functionality of any other aspects of the system. The single unit can thus also be scalable with the ability to be added to as additional modules and/or additional functionality of existing modules are desired and/or improved upon.

A computer system can also include any of a variety of other software and/or hardware components, including by way of non-limiting example, operating systems and database management systems. Although an exemplary computer system is depicted and described herein, it will be appreciated that this is for sake of generality and convenience. In other embodiments, the computer system may differ in architecture and operation from that shown and described here.

Robotic Surgical Systems

The systems, devices, and methods disclosed herein can be implemented using a robotic surgical system. Various embodiments of robotic surgical systems are described in further detail in U.S. Pat. No. 8,831,782 filed Jul. 15, 2013 entitled "Patient-Side Surgeon Interface For A Teleoperated Surgical Instrument," Intl. Pat. Pub. No. WO2014151621 filed Mar. 13, 2014 entitled "Hyperdexterous Surgical System," Intl. Pat. Pub. No. WO2014151952 filed Mar. 13, 2014 entitled "Compact Robotic Wrist," and U.S. Pat. Pub. No. 2012/0158013 filed Dec. 17, 2010 entitled "Surgical System And Methods For Mimicked Motion," which are hereby incorporated by reference in their entireties.

As will be appreciated by a person skilled in the art, electronic communication between various components of a robotic surgical system can be wired or wireless. A person skilled in the art will also appreciate that all electronic communication in the system can be wired, all electronic communication in the system can be wireless, or some portions of the system can be in wired communication and other portions of the system can be in wireless communication.

Figure 3:
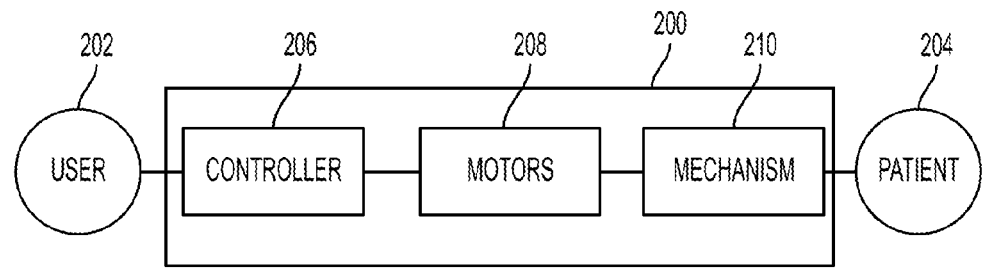
FIG. 3 is a schematic view of one embodiment of a robotic surgical system configured to be operated by a user and to be used during performance of a surgical procedure on a patient.

FIG. 3 illustrates an embodiment of a robotic surgical system 200 configured to be used by a user 202 (e.g., a surgeon, a surgical assistant, etc.) during performance of a surgical procedure on a patient 204. As in this illustrated embodiment, the robotic surgical system 200 can include a controller 206, motors 208, and a movement mechanism 210. The controller 206 can be configured to receive an input from the user 202 requesting movement, relative to the patient 204, of a surgical instrument coupled to the movement mechanism 210. The controller 206 can be configured to cause the motors 208 to drive movement of the movement mechanism 210, thereby causing the movement of the surgical instrument requested by the user 202. Although the illustrated robotic surgical system 200 includes a plurality of motors 208, a robotic surgical system can include a single motor. Similarly, although the illustrated robotic surgical system 200 includes a single controller 206 and a single movement mechanism 210, a robotic surgical system can include a plurality of controllers and/or a plurality of movement mechanisms.

In an exemplary embodiment, the movement mechanism 210 can include an arm. The arm can be configured to move so as to cause movement of a surgical instrument coupled thereto in any one or more of the three translational directions (surge, heave, and sway) and in any one or more of the three rotational directions (roll, pitch, and yaw) in response to control by the controller 206. In an exemplary embodiment, the arm can be configured to provide a plurality of degrees of freedom. More than six degrees of freedom can be provided in a variety of ways, as mentioned above and as will be appreciated by a person skilled in the art. In general, the arm can include a mechanical member configured to move in response to an input to the system 200 from the user 202. The user's input can be configured to cause the controller 206 to transmit an electronic signal to the motors 208 that causes the motors 208 to provide a force (e.g., torque) to the arm, thereby causing movement of the arm. The arm can include a plurality of members jointed together, which can facilitate movement of the arm in a plurality of degrees of freedom via bending, twisting, etc. at various ones of the joints.

The arm can include an electromechanical arm. The electromechanical arm can include one or more mechanical members configured to move in response to an electronic input. Examples of mechanical members that can form the arm include elongate shafts, coupling mechanisms (e.g., clips, magnets, snap fit mechanisms, shaped members configured to seat an instrument therein by interference fir or press fit, clamps, protrusions configured to be seated in corresponding depressions formed in a surgical instrument, depressions configured to receive therein corresponding protrusions extending from a surgical instrument, etc.) configured to removably and replaceably couple a surgical instrument to the arm, and joints (e.g., hinges, gimbals, etc.).

Figure 4:
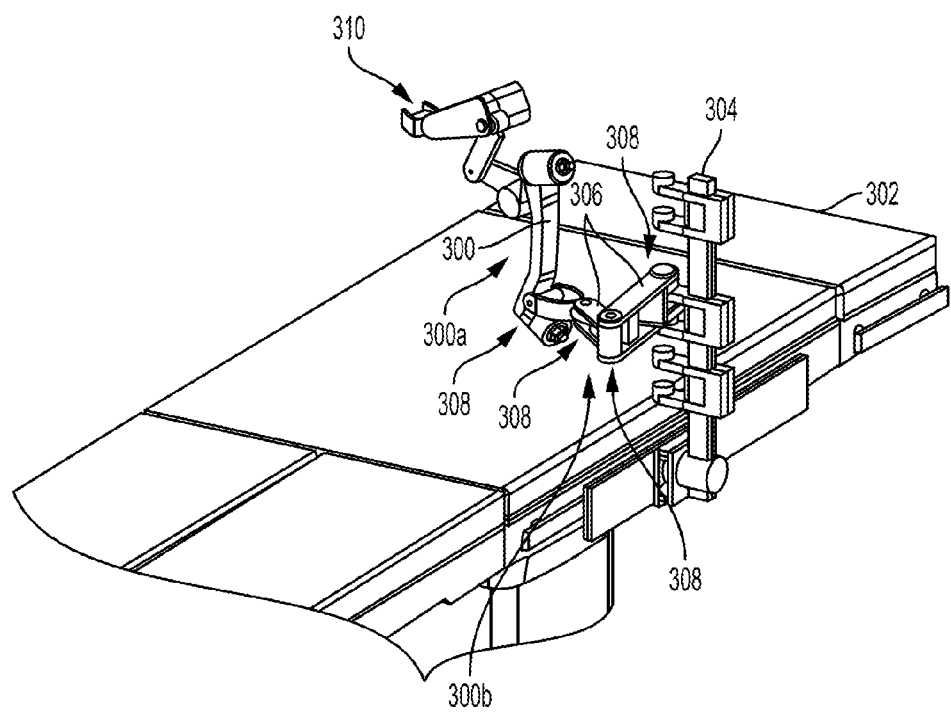
FIG. 4 is a perspective view of one embodiment of an arm of a robotic surgical system, the arm being mounted to a surgical table.
Figure 5:
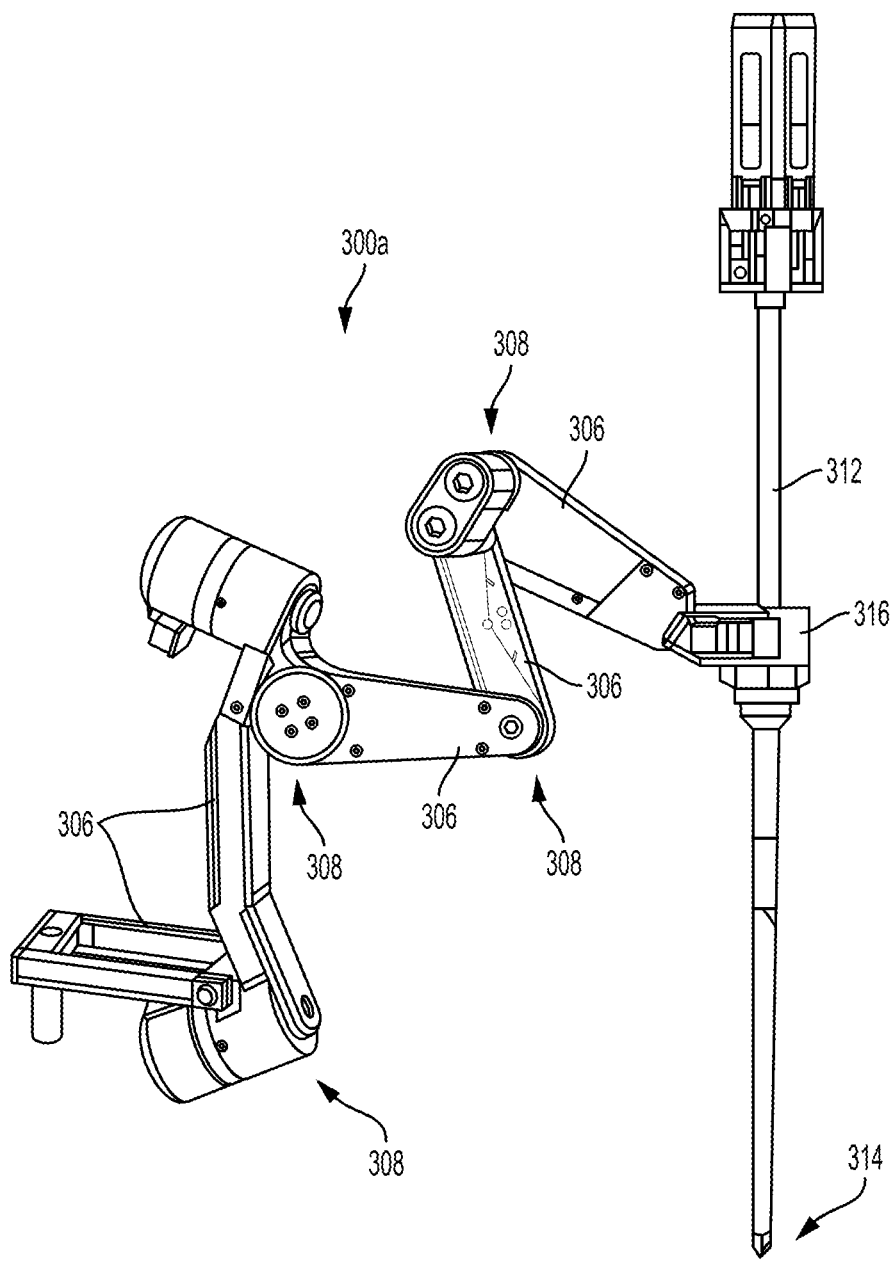
FIG. 5 is a perspective view of an active portion of the arm of FIG. 4.

FIGS. 4 and 5 illustrate an embodiment of an arm 300 in the form of an electromechanical arm. The arm 300 is mounted to a surgical table 302 using a frame 304 in the illustrated embodiment of FIG. 4, but the arm 300 can be mounted to any of a variety of stationary items, a wall, a table, a cart, the ceiling, etc., in any of variety of ways to help stabilize the arm 300 for use during a surgical procedure. The arm 300 can include an active portion 300a configured to be actively controlled, e.g., configured to move in response to electronic input, and a passive portion 300b configured to be passively controlled, e.g., configured to move in response to hand or other manual movement thereof. The passive portion 300b can lack motors or other electrical features, while the active portion 300a can include motors and other electrical features, such as associated with the joints, to facilitate electronic control thereof. In at least some embodiments, an arm can lack a passive portion so as to be configured to be entirely actively controlled. While the active and passive portions 300a, 300b are sometimes referred to herein as components of a single arm, a person skilled in the art will appreciate that the active portion 300a and the passive portion 300b can be separate arms that are matable to each other.

The arm 300 can, as in this illustrated embodiment, include a plurality of mechanical members 306, a plurality of joints 308, and a coupling mechanism 310. Adjacent ones of the mechanical members 306 can be attached together at one of joints 308. In this illustrated embodiment, the active portion 300a of the arm 300 includes five mechanical members 306 and four joints 308, the passive portion 300b of the arm 300 includes two mechanical members 306 and three joints 308, and the arm 300 includes another joint 308 between the active and passive portions 300a, 300b, but arms can have any number of mechanical members and associated joints in its active and passive portions.

As shown in FIG. 5, the arm 300, e.g., the active portion 300a thereof, can be configured to removably and replaceably couple to a surgical instrument 312 via the coupling mechanism 310. A distal end 314 of the instrument 312 can be configured to be advanced into a body of a patient, e.g., through an incision, through a natural orifice, etc. The instrument's distal end 314 can thus include a working end of the instrument 312 configured to facilitate performance of the surgical procedure within the patient. The instrument's distal end 314 can include an end effector, e.g., forceps/graspers, needle drivers, scissors, electrocautery hooks, staplers, clip appliers/removers, suction tools, irrigation tools, etc. As in this illustrated embodiment, the instrument 312 can be advanced into a patient's body through a cannula 316 (e.g., a trocar, an introducer tube, etc.). The coupling mechanism 310 is shown in FIG. 5 coupled to the cannula 316, which has the surgical instrument 312 advanced therethrough.

Aspects of the arm 300 and the frame 304 are further described in previously mentioned Intl. Pat. Pub. No. WO2014151621 filed Mar. 13, 2014 entitled "Hyperdexterous Surgical System" and Intl. Pat. Pub. No. WO2014151952 filed Mar. 13, 2014 entitled "Compact Robotic Wrist."

Figure 6:
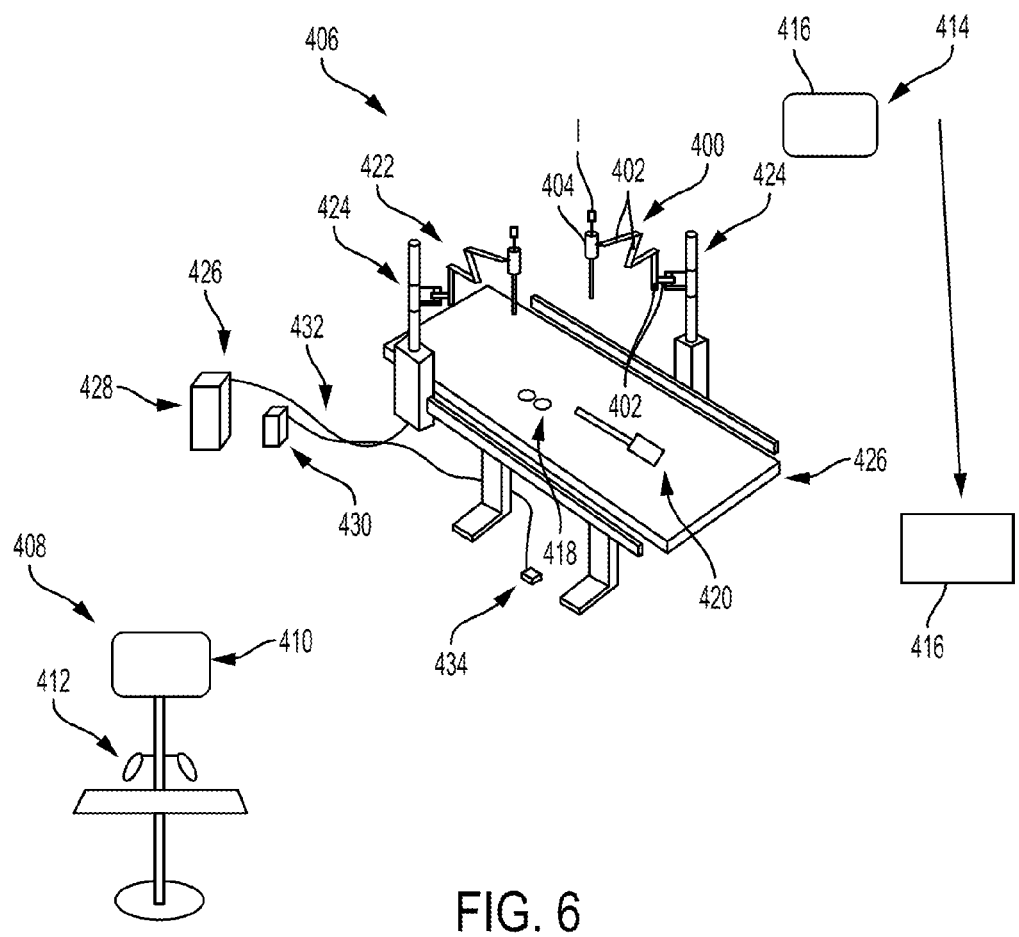
FIG. 6 is a perspective view of one embodiment of a robotic surgical system.

FIG. 6 illustrates another embodiment of an arm 400 in the form of an electromechanical arm. The arm 400 can generally be configured and used similar to the arm 300 of FIGS. 4 and 5. The arm 400 can include a plurality of mechanical members 402, a plurality of joints between adjacent ones of the arms 402, and a coupling mechanism 404 configured to removably and replaceably couple to a surgical instrument I. The arm 400 includes five mechanical members 402 and four joints in this illustrated embodiment, but as mentioned above, arms can have any number of mechanical members and associated joints.

Figure 7:
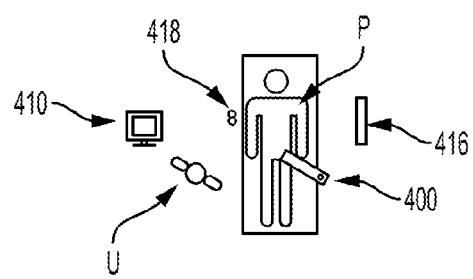
FIG. 7 is a schematic view of one embodiment of the robotic surgical system of FIG. 6 in use during performance of a surgical procedure on a patient.
Figure 8:
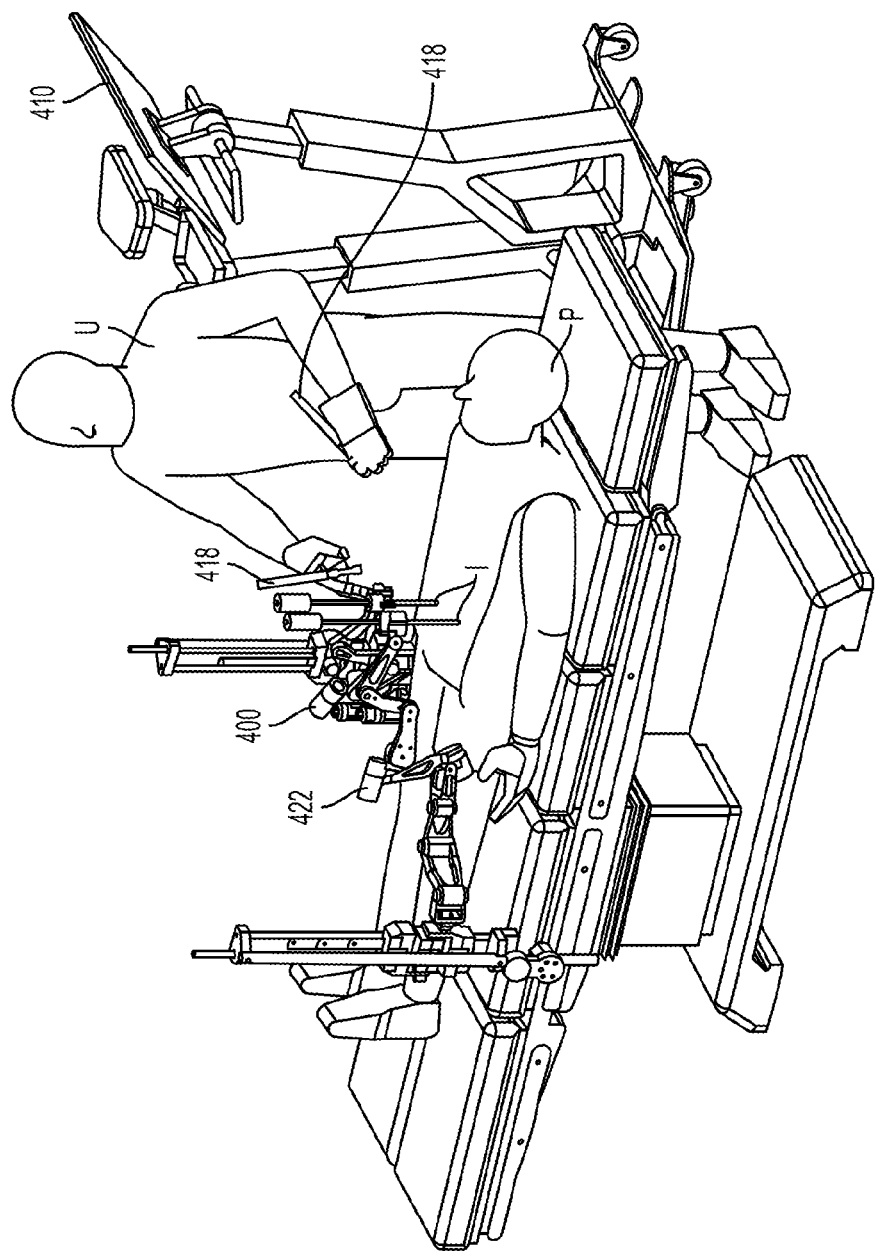
FIG. 8 is a perspective view of the robotic surgical system of FIG. 7 in use during performance of the surgical procedure on a patient.

As shown in FIGS. 6 and 7, the arm 400 can be included in a robotic surgical system 406 configured to facilitate performance of a surgical procedure on a patient P. FIG. 8 shows an example of the system 406 in use. As in this illustrated embodiment, the system 406 can include a user interface sub-system 408 that can include at least one display 410 configured to display information thereon to a user U, at least one user input device 412 configured to receive a user input thereto to control movement of the arm 400, a visualization system 414 that can include at least one display 416 configured to display thereon image(s) of a surgical procedure being performed using the system 406, a freely movable user input device 418 (shown as pinchers in this illustrated embodiment) configured to receive a user input thereto to control movement of the arm 400 and configured to be freely moved around by the user U (e.g., handheld and moved around any space in or near an operating room, etc.), an additional arms 422 that can be configured and used similar to the arm 400, and a control system 426 configured to facilitate control of the arms 400, 422 by translating user inputs to the user input devices 412, 418, e.g., manual movement of a user input device, movement indicated by touch on a touch screen, etc., to one or both of the arms 400, 422 as appropriate. The system 406 in this illustrated embodiment includes two arms 400, 422, but it can include another number of arms, e.g., three, four, etc. The at least one display 410 of the user interface sub-system 408 can be configured as a user input device, e.g., as a touchscreen configured to receive user touch input thereon. The user interface sub-system 408 can be in the same room as the patient P, or it can be in a different room.

The control system 426 can, as in this illustrated embodiment, include at least one computer 428, one or more cables 430, and at least one power supply 432. The computer 428 can include at least one processor (not shown). As mentioned above, at least some embodiments of control systems can be at least partially wireless, in which case at least some of the cables 430 need not be present. The robotic surgical system 406 can include at least one foot pedal 434 coupled to the computer 428 via one of the cables 430, which can allow the foot pedal 434 to serve as a user input device. The robotic surgical system 406 can include at least one knee control (not shown) coupled to the computer 428 via one of the cables 430, similar to a knee control of a sewing machine, which can allow the knee control to serve as a user input device.

The robotic surgical system 406 can include a frame 424 for each of the arms 400, 422. The frames 424 in this illustrated embodiment are each mounted to a surgical table 426, but as mentioned above, frames can be mounted elsewhere. The frame 424 in this illustrated embodiment includes a vertical extension movably coupled to a rail mounted to the table 426. The vertical extension can be configured to move along the rail, thereby facilitating positioning of the arms 400, 422 relative to the patient P.

One or more manually operated surgical instruments 420, e.g., instruments not under the control of the robotic surgical system 406, can be used to perform the surgical procedure being performed on the patient P.

Aspects of the robotic surgical system 406 are further described in previously mentioned Intl. Pat. Pub. No. WO2014151621 filed Mar. 13, 2014 entitled "Hyperdexterous Surgical System."

Figure 9:
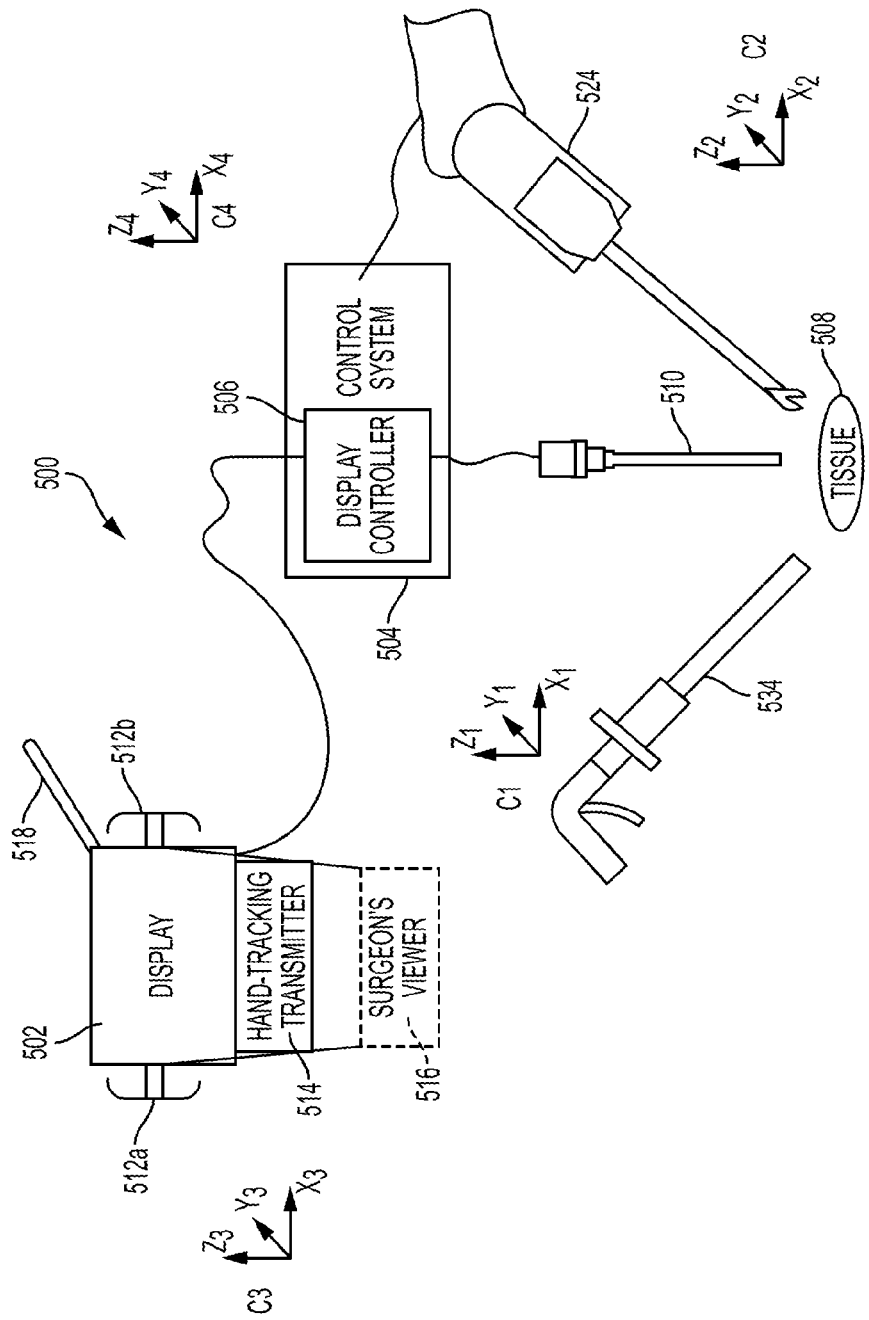
FIG. 9 is a schematic and perspective view of another embodiment of a robotic surgical system.

FIG. 9 illustrates another embodiment of a robotic surgical system 500. As in this illustrated embodiment, the robotic surgical system 500 can include a display 502 and a control system 504 configured to be in electronic communication with the display 502. The display 502 and the control system 504 are in wired electronic communication in this illustrated embodiment, but the electronic communication can be wireless. The control system 504 can include a computer system including a display controller 506 configured to facilitate the display of images on the display 502, such as images of tissue 508 visualized by an endoscope 510 coupled to the control system 504. The display 502 can be coupled to handles 512a, 512b configured to facilitate manual movement of the display 502, a hand-tracking transmitter 514 configured to generate a field (e.g., an electromagnetic field, an optical field (e.g., light beams), etc.), a surgeon's viewer 516 (e.g., glasses, etc.) configured to facilitate three-dimensional (3-D) viewing of 3-D images shown on the display 502, and a boom 518 configured to mount the display 502 to a stable surface (e.g., a wall, a table, etc.). The display 502 can be configured to show two-dimensional (2-D) and/or 3-D images.

Figure 10:
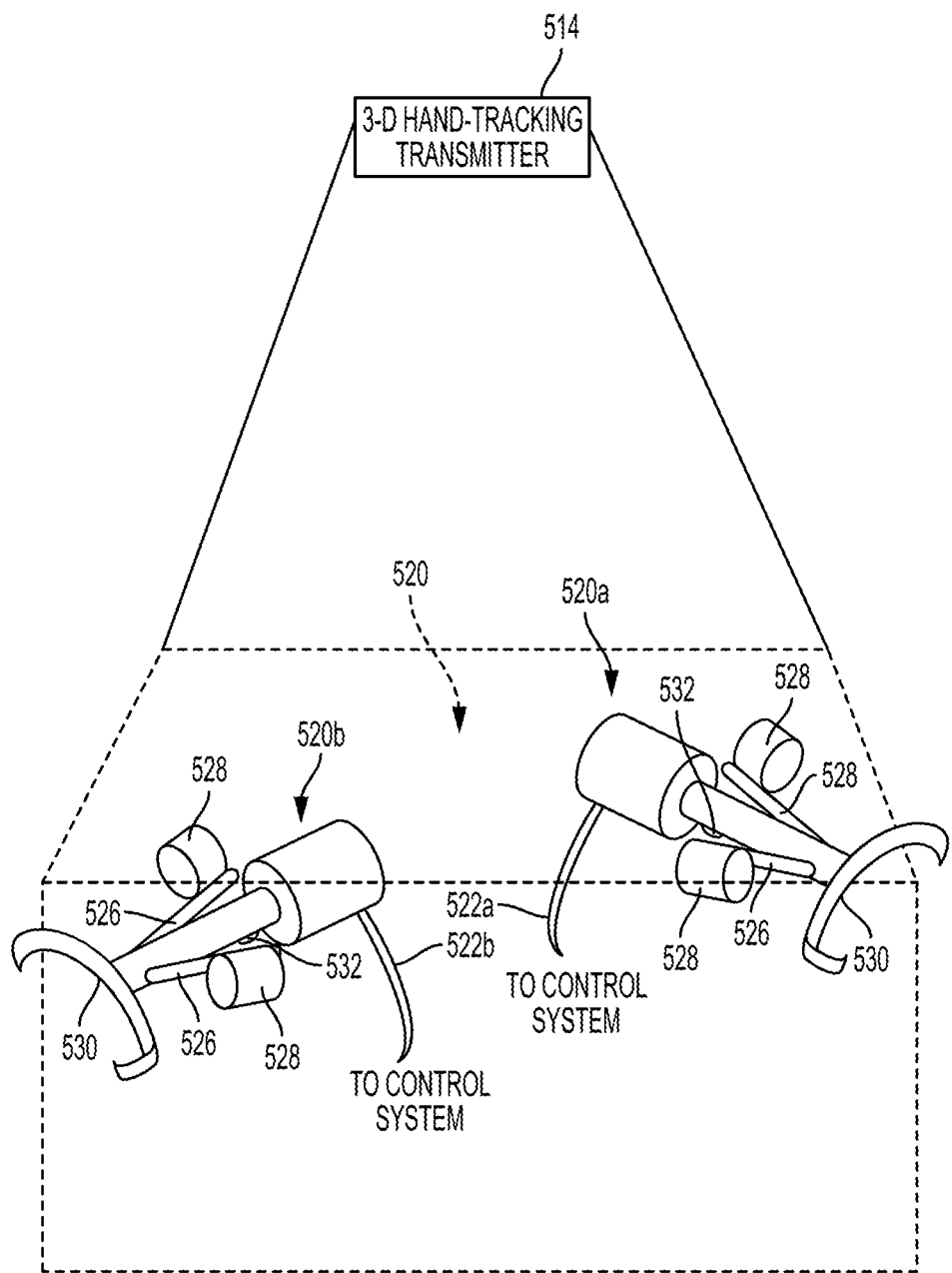
FIG. 10 is a perspective view of one embodiment of a master tool in a field generated by a transmitter of the robotic surgical system of FIG. 9.

Movement of a user-controlled master tool 520, an embodiment of which is illustrated in FIG. 10, in the field generated by the transmitter 514 can be configured to provide sensed spatial position and orientation information in a 3-D coordinate system. The master tool 520 can be configured to transmit the spatial position and orientation information to the control system 504, such as by cables 522a, 522b. The control system 504, e.g., a processor thereof, can be configured to receive the transmitted spatial position and orientation information and, in response thereto, cause a slave tool 524 to move in accordance with the user's movement of the master tool 520. The robotic surgical system 500 can thus allow control of the slave tool 524 via the master tool 520. The master tool 520 in this illustrated embodiment includes first and second master tool grips 520a, 520b that each include a plurality of levers 526, a plurality of finger loops 528, a palm rest 530, and a mode control button 532, but the master tool 520 can have a variety of other configurations, as will be appreciated by a person skilled in the art. The robotic surgical system 500 can include any number of master tools and any number of slave tools each configured to be controlled by the master tool(s).

One or more manually operated surgical instruments 534 can be used to manipulate the tissue 508 in addition to the slave tool 524 that can manipulate the tissue 508.

FIG. 9 illustrates first, second, third, and fourth coordinate systems C1, C2, C3, C4 representing local coordinates that specify the respective position and orientation of the portion of the system 500 with which they are associated. The first coordinate system C1 is associated with the manually operated surgical instrument 534. The second coordinate system C2 is associated with the slave tool 524. The third coordinate system C3 is associated with a user (not shown) visualizing the display 502, and hence also with the master tool 520 configured to be manipulated by the user. The fourth coordinate system C4 is associated with the control system 506, and hence also with images that the control system 506 causes to be displayed on the display 502. In general, the control system 506 can be configured to map and translate the third coordinate system C3 into the second coordinate system C2, e.g., map and translate movement of the master tool 520 to movement of the slave tool 524. The control system 506 can be configured to always orient the display 502 so that the first, second, and third coordinate systems C1, C2, C3 are aligned to the third coordinate system C3. For example, if the user is holding the master tool 520, e.g., one of the first and second master tool grips 520a, 520b, in one of his/her hands and moves that hand to his/her right, thereby moving the held master tool 520 to the right, the control system 506 can be configured to correspondingly cause a working end of the slave tool 524 to move to the right. This movement can be accomplished by the control system 506 causing an arm to which the slave tool 524 is coupled, similar to the arms discussed herein, to move. This movement of the slave tool 523 can "correct" for pivoting of a trocar (not shown) through which the slave tool 524 may be inserted to access the tissue 508.

Aspects of the robotic surgical system 500 are further described in previously mentioned U.S. Pat. No. 8,831,782 filed Jul. 15, 2013 entitled "Patient-Side Surgeon Interface For A Teleoperated Surgical Instrument."

Figure 11:
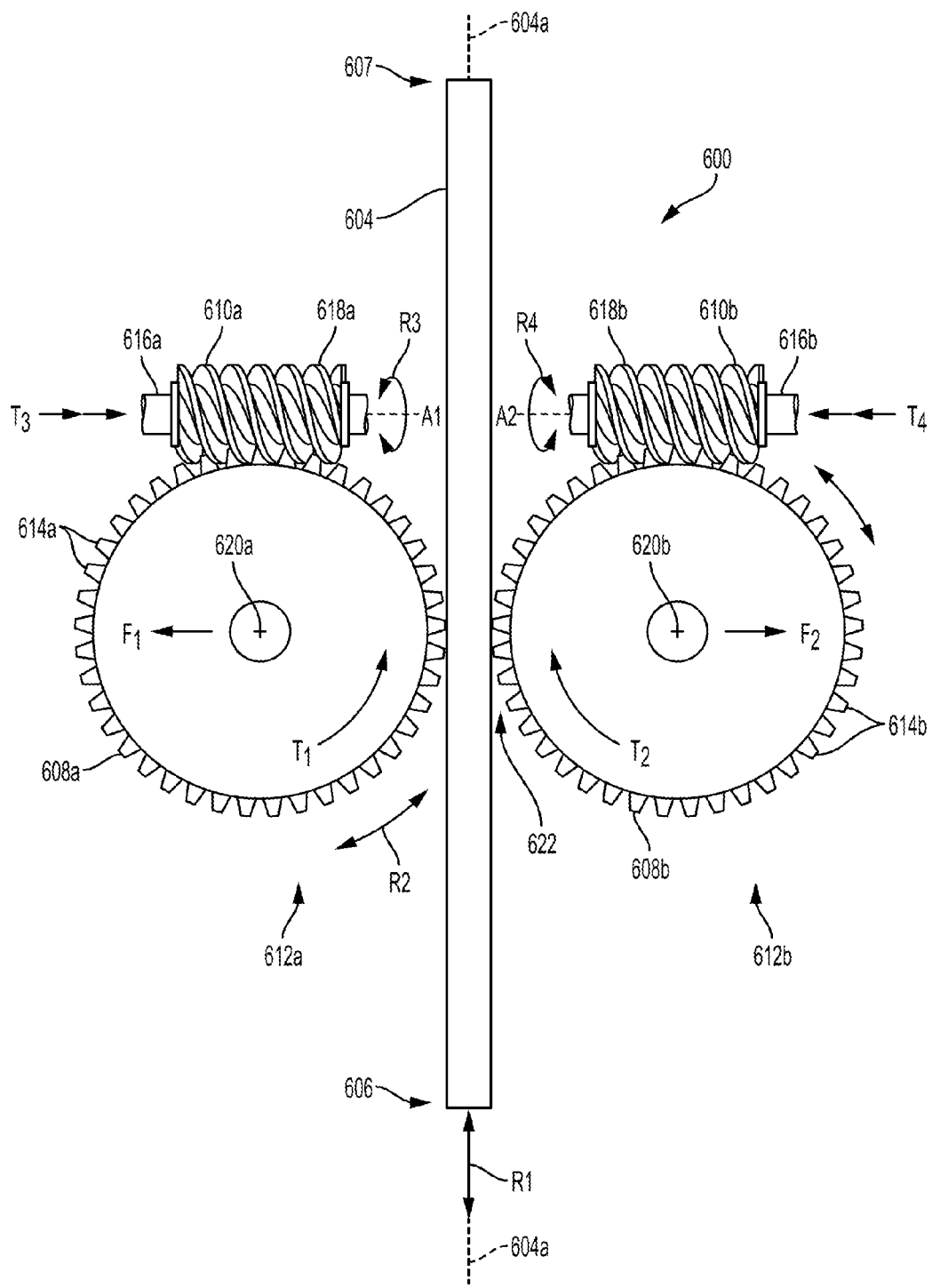
FIG. 11 is a side view of one embodiment of a movement assembly of a robotic surgical system, the movement assembly being coupled to a shaft of a surgical instrument.

As mentioned above, at least some of the methods, systems, and devices for controlling movement of a robotic surgical system provided herein can include a movement assembly (also referred to herein as a "tool controller" or a "tool driver") configured to facilitate movement of surgical instrument coupled to the robotic surgical system. FIG. 11 illustrates one embodiment of a movement assembly 600 of a robotic surgical system configured to provide a lateral force to a surgical instrument 602 coupled to the robotic surgical system. The surgical instrument 602 is partially illustrated in FIG. 11, with only a shaft 604 of the instrument 602 illustrated in FIG. 11. The surgical instrument 602 can generally be configured and used similar to surgical instruments discussed herein and can have an end effector at a distal end 606 of the shaft 604 and a handle at a proximal end 607 of the shaft 604. The robotic surgical system can generally be configured and used similar to the robotic surgical system 200 of FIG. 3, e.g., can include at least one controller, at least one motor, and at least one movement mechanism. The movement assembly 600 can be operatively coupled to a movement mechanism, e.g., an electromechanical arm, of the robotic surgical system. In an exemplary embodiment, the movement assembly 600 can be fixed to the movement mechanism so as to be non-removable therefrom.

The controller of the robotic surgical system can be configured to receive an input from a user (not shown) requesting movement, relative to a patient (not shown), of the instrument 602. The user can provide the input using a user input device (not shown), as discussed herein. The controller can be configured to cause the motor (not shown) of the robotic surgical system to drive movement of the movement mechanism and/or the movement assembly 600, thereby causing movement of the surgical instrument 602 coupled thereto. The movement mechanism can be configured to move, as discussed above, to cause various movements of the surgical instrument 602, such as angular adjustments of the instrument 602 relative to the patient, actuation of the end effector, etc. The movement assembly 600 can be configured to move, as discussed further below, to cause translational movement of the surgical instrument 602 in opposed proximal and distal directions along a longitudinal axis 604A of the instrument's shaft 604, as indicated by arrow R1.

As in this illustrated embodiment, the movement assembly 600 can include a pair of opposed rollers or wheels 608a, 608b and a pair of opposed worm gears 610a, 610b. The first roller 608a can be operatively coupled to the first worm gear 610a such that movement of the first worm gear 610a can cause movement of the first roller 608a. Similarly, the second roller 608b can be operatively coupled to the second worm gear 610b such that movement of the second worm gear 610b can cause movement of the second roller 608b. The first roller 608a and the first worm gear 610a can together define a first worm drive 612a, and the second roller 608b and the second worm gear 610b can together define a second worm drive 612b. The movement assembly 600 can thus include two opposed worm drives 612a, 612b.

The first wheel 608a can have teeth 614a around a circumference thereof that face outwardly, e.g., extend radially outward. The first wheel 608a can be configured to rotate about a center point 620a thereof, as shown by arrow R2. The first worm gear 610a can include a worm shaft 616a and have a thread 618a extending therearound. The first worm gear 610a can be configured to rotate about a longitudinal axis A1 of the worm shaft 616a, as shown by arrow R3. The first worm gear's thread 618a can be operatively engaged with the teeth 614a of the first wheel 608a. Movement of the first worm gear 610a can cause movement of the first wheel 608a due to the threaded engagement of the thread 618a and the teeth 614a. Thus, rotation of the first worm gear 610a about the longitudinal axis A1 of the worm shaft 616a can cause the first wheel 608a to rotate about the first wheel's center point 620a. In other words, torque $T_3$ of the first worm gear 610a, e.g., of the worm shaft 616a, can be converted into torque $T_1$ of the first wheel 608a. The torques $T_1$, $T_3$ of the first worm drive 612a are shown in FIG. 11 for clockwise rotation of the first worm gear 610a that causes counterclockwise rotation of the first wheel 608a, but similar, opposite torques are produced for counterclockwise rotation of the first worm gear 610a that causes clockwise rotation of the first wheel 608a. The first worm gear 610a can be configured to be driven by one or more of the motors of the robotic surgical system.

The second wheel 608b and the second worm gear 610b can be configured similar to the first wheel 608a and the first worm gear 610a. The second wheel 608b can have teeth 614b around a circumference thereof that face outwardly. The second wheel 608b can be configured to rotate about a center point 620b thereof, as shown by arrow R4. The second worm gear 610b can include a worm shaft 616b and have a thread 618b extending therearound. The second worm gear 610b can be configured to rotate about a longitudinal axis A2 of the worm shaft 616b, as shown by arrow R5. The second worm gear's thread 618b can be operatively engaged with the teeth 614b of the second wheel 608b. Movement of the second worm gear 610b can cause movement of the second wheel 608b due to the threaded engagement of the thread 618b and the teeth 614b. Thus, rotation of the second worm gear 610b about the longitudinal axis A2 of the worm shaft 616b can cause the second wheel 608b to rotate about the second wheel's center point 620b. In other words, torque $T_4$ of the second worm gear 610b, e.g., of the worm shaft 616b, can be converted into torque $T_2$ of the second wheel 608b. The torques $T_2$, $T_4$ of the second worm drive 612b are shown in FIG. 11 for counterclockwise rotation of the second worm gear 610b that causes clockwise rotation of the second wheel 608b, but similar torques are produced for clockwise rotation of the second worm gear 610b that causes counterclockwise rotation of the second wheel 608b. The second worm gear 610b can be configured to be driven by the one or more of the motors of the robotic surgical system.

The first and second worm drives 612a, 612b can be configured to be simultaneously driven, e.g., simultaneously caused to move by the robotic surgical system's motor(s), in opposite directions. In other words, one of the first and second worm gears 610a, 610b can be configured to be driven to rotate in a counterclockwise direction so as to cause clockwise movement of its associated one of the wheels 608a, 608b, and the other one of the first and second worm gears 610a, 610b can be configured to be driven to rotate in a clockwise direction so as to cause counterclockwise movement of its associated one of the wheels 608a, 608b. This opposite movement of the first and second worm drives 612a, 612b can facilitate selective proximal and distal translation of the instrument's shaft 604, as discussed further below.

The first and second worm drives 612a, 612b, e.g., the first wheel 608a of the first worm drive 612a and the second wheel 608b of the second worm drive 612b, can be configured to engage the shaft 604 of the instrument 602 therebetween. The first and second wheels 608a, 608b can be spaced a distance apart from one another to define a gap 622 therebetween. The shaft 604 can be configured to be inserted into the gap 622 so as to be engaged between the first and second wheels 608a, 608b.

The gap 622 can have a fixed width, e.g., the space between the first and second wheels 608a, 608b can be fixed. The fixed width of the gap 622 can correspond to a particular instrument shaft diameter size such that the movement assembly 600 can be configured to accommodate an instrument shaft 604 having a specific diameter. The movement assembly 600 can thus be configured to securely grasp instrument shafts having that specific, predetermined diameter. Alternatively, the gap 622 can have a variable width, e.g., the space between the first and second wheels 608a, 608b can be configured to change. The gap 622 having a variable width can allow the movement assembly 600 to accommodate instrument shafts of various diameters, which may allow the robotic surgical system to be compatible with many different surgical instruments, may allow the robotic surgical system to be compatible with shafts having non-standard size diameters, may not limit the robotic surgical system to use with only one size of surgical instrument or to use with a limited number of predetermined sizes of surgical instruments. The width of the gap 622 can be configured to be manually adjusted, such as by moving the first and second wheels 608a, 608b to be separated a desired distance from one another and locking the first and second wheels 608a, 608b in position using a locking mechanism such as a thumbscrew, a clamp, a depressible peg seatable in a selected one of a plurality of holes, etc. The gap 622 can thus be adjusted to accommodate a selected shaft diameter size, which may facilitate use of a variety of different surgical instruments with the movement assembly 600. Alternatively, the width of the gap 622 can be configured to be automatically adjusted, such as by the first and second wheels 608a, 608b being spring-mounted and biased toward each other. The gap 622 being automatically adjustable may allow the movement assembly 600 to be used with a variety of different surgical instruments and without the gap 622 having to be pre-adjusted by a user to the correct width for a selected surgical instrument.

The teeth 614a, 614b of the first and second wheels 608a, 608b can be configured to engage the shaft 604 of the instrument 602 positioned between the wheels 608a, 608b. The teeth 614a, 614b can include a gripping feature configured to facilitate gripping of the shaft 604 by increasing a friction force therebetween. Examples of gripping features include a textured surface and a sticky coating. The teeth 614a, 614b of the first and second wheels 608a, 608b can thus, as in this illustrated embodiment, be configured to operatively engage both the shaft 604 and their associated one of the worm gears 610a, 610b. In at least some embodiments, the shaft 604 can include a gripping feature (e.g., a textured surface such as grit or such as gear-like teeth configured to engage the teeth 614a, 614b, a sticky coating, etc.) configured to facilitate gripping of the shaft 604 by the wheels 608a, 608b. In at least some embodiments, the teeth 614a, 614b of the first and second wheels 608a, 608b can be configured to operatively engage their associated one of the worm gears 610a, 610b but not operatively engage the shaft 604. Instead, another surface of the wheels 608a, 608b can be configured to engage the shaft 604. This other surface can be adjacent to the teeth 614a, 614b and can be, for example, a smooth surface, a textured surface (e.g., including gear-like teeth, including grit, etc.), or an elastomeric surface.

The rotation of the first worm gear 610a can produce a reaction force $F_1$ in the first wheel 608a in addition to the torque force $T_1$. Similarly, the rotation of the second worm gear 610b can produce a reaction force $F_2$ in the second wheel 608b in addition to the torque force $T_2$. The reaction forces $F_1$, $F_2$ can generally be considered "waste" forces produced as byproducts of the "non-waste" torque forces $T_1$, $T_2$. The reaction forces $F_1$, $F_2$ can urge the wheels 608a, 608b away from one another, thereby increasing a width of the gap 622, which may reduce grip on the shaft 604 and accordingly increase a chance of the shaft 604 undesirably slipping. The wheels 608a, 608b including a gripping feature, the shaft 604 including a gripping feature, and the wheels 608a, 608b being biased toward one another can each help offset effect of the reaction forces $F_1$, $F_2$ and consequently help prevent undesirable slippage of the shaft 604. The movement assembly 600 can thus be configured to make use of the "waste" forces reaction forces $F_1$, $F_2$ to help grip the shaft 604. The reaction forces $F_1$, $F_2$ are shown in FIG. 11 for clockwise rotation of the first worm gear 610a that causes counterclockwise rotation of the first wheel 608a and counterclockwise rotation of the second worm gear 610b that causes clockwise rotation of the second wheel 608b, but similar reaction forces $F_1$, $F_2$ are produced for counterclockwise rotation of the first worm gear 610a that causes clockwise rotation of the first wheel 608a and clockwise rotation of the second worm gear 610b that causes counterclockwise rotation of the second wheel 608b.

When the shaft 604 is positioned within the gap 622 and is engaged by the first and second wheels 608a, 608b, the movement of the first and second worm drives 612a, 612b can cooperate to cause translational movement of the shaft 604 (e.g., as shown by arrow R1) and hence cause translational movement of the instrument 602. The rotation of the worm drives 612a, 612b (e.g., the rotation of the worm gears 616a, 616b and the rotation of the wheels 608a, 608b) can thus be translated into translational movement of the shaft 604, and hence of the instrument 602. The first and second wheels 608a, 608b can generally feed the shaft 604 proximally or distally, the direction depending on the directional rotation of the wheels 608a, 608b, similar to conveyor belt movement.

Figure 12:
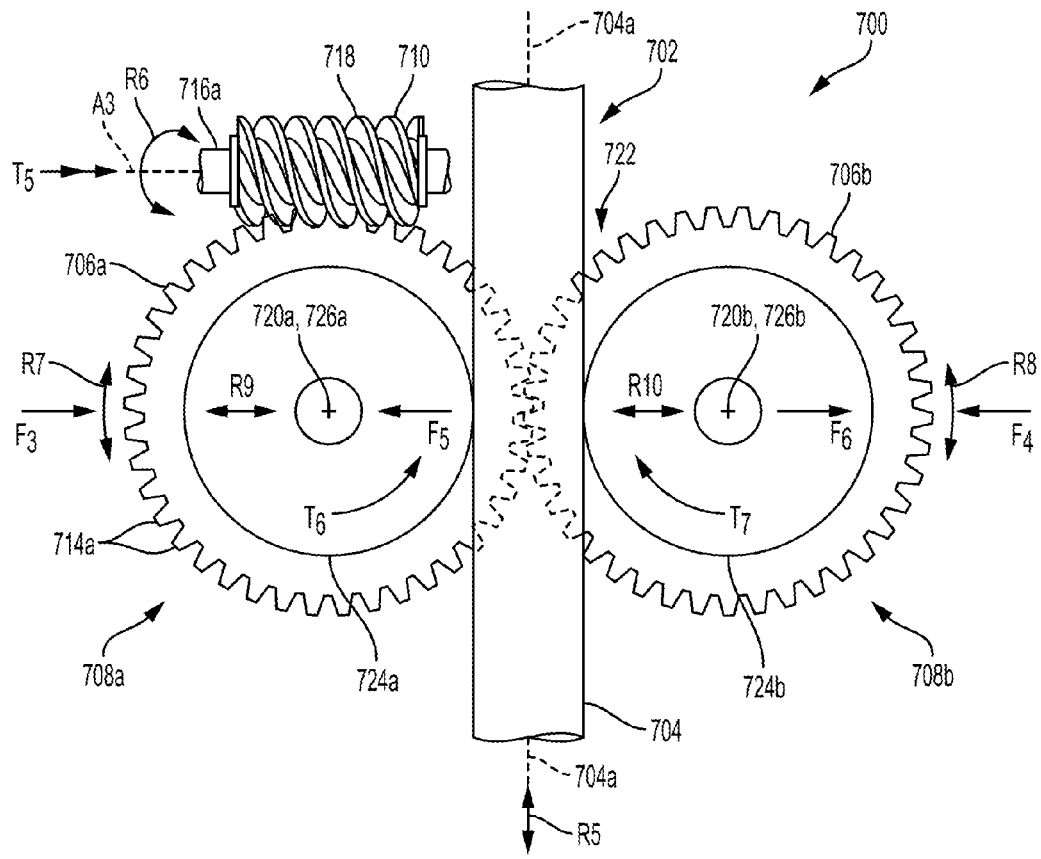
FIG. 12 is a side view of another embodiment of a movement assembly of a robotic surgical system, the movement assembly being coupled to a shaft of a surgical instrument.

FIG. 12 illustrates another embodiment of a movement assembly 700 of a robotic surgical system configured to provide a lateral force to a surgical instrument 702 coupled to the robotic surgical system. The surgical instrument 702 is partially illustrated in FIG. 12, with only a portion of a shaft 704 of the instrument 702 illustrated in FIG. 11. The surgical instrument 702 can generally be configured and used similar to surgical instruments discussed herein and can have an end effector at a distal end of the shaft 704 and a handle at a proximal end of the shaft 704. The robotic surgical system can generally be configured and used similar to the robotic surgical system 200 of FIG. 3, e.g., can include at least one controller, at least one motor, and at least one movement mechanism. The movement assembly 700 can be operatively coupled to a movement mechanism, e.g., an electromechanical arm, of the robotic surgical system. In an exemplary embodiment, the movement assembly 700 can be fixed to the movement mechanism so as to be non-removable therefrom.

Similar to that discussed above with respect to the movement mechanism 600 of FIG. 11, the controller of the robotic surgical system including the movement mechanism 700 of FIG. 12 can be configured to receive an input from a user (not shown) requesting movement, relative to a patient (not shown), of the instrument 702 and can be configured to cause the motor (not shown) of the robotic surgical system to drive movement of the movement mechanism and/or the movement assembly 700, thereby causing movement of the surgical instrument 702 coupled thereto. The movement mechanism can be configured to move, as discussed above, to cause various movements of the surgical instrument 702, such as angular adjustments of the instrument 702 relative to the patient, actuation of the end effector, etc. The movement assembly 700 can be configured to move, as discussed further below, to cause translational movement of the surgical instrument 702 in opposed proximal and distal directions along a longitudinal axis 704A of the instrument's shaft 704, as indicated by arrow R5.

As in this illustrated embodiment, the movement assembly 700 can include a pair of opposed rollers or wheels 708a, 708b and a single worm gear 710. The first wheel 708a can include a first gear roller or wheel 706a and a first floating roller or wheel 724a. The first gear wheel 706a can be operatively coupled to the worm gear 710 such that movement of the worm gear 710 can cause movement of the first gear roller 706a. The first floating wheel 724a can be operatively coupled to the first gear wheel 706a such that movement of the first gear wheel 706a can cause movement of the first floating wheel 724a. Thus, movement of the worm gear 710 can cause movement of both the first gear wheel 706a and the first floating wheel 724a. The first gear wheel 706a and the first floating wheel 724a can thus be configured to move simultaneously due to the worm gear's movement.

The first floating wheel 724a can also be configured to move translationally, as shown by arrow R9. The translational movement of the first floating wheel 724a can be relative to the first gear wheel 706a such that the first floating wheel 724a can "float" relative to the first gear wheel 706a. The translational movement of the first floating wheel 724a can be independent of the rotational movement of the first floating wheel 724a. A center shaft mount at a center point 726a of the first floating wheel 724a can be linearly movable to allow for the first floating wheel's translational movement, such as by the center shaft mount being a bendable and/or elastic member. In other embodiments, the translational movement of the first floating wheel 724a can be provided using another type of mount, such as a slotted axle bushing. The center point 726a of the first floating wheel 724a is aligned with a center point 720a of the first gear wheel 706a in FIG. 12, but the center point 726a can become laterally offset therefrom as the first floating wheel 724a floats. The translational movement of the first floating wheel 724a can be substantially perpendicular to the longitudinal axis 704A of the shaft 704, which may facilitate gripping of the shaft 704 by the movement assembly 700 by allowing the first floating wheel 724a to move toward the shaft 704 and/or may help the movement assembly 700 accommodate surgical instruments of various diameters. A person skilled in the art will appreciate that the translational movement of the first floating wheel 724a may not be precisely perpendicular to the longitudinal axis 704A of the shaft 704 for any one or more reasons, e.g., manufacturing tolerances of the shaft 704, manufacturing tolerances of the first floating wheel 724a, accuracy of measurement devices, etc., but nevertheless be considered to be substantially perpendicular thereto.

The second roller 708b can include a second gear roller or wheel 706b and a second floating roller or wheel 724b. The second gear wheel 706b can be operatively coupled to the first gear wheel 706a, e.g., via enmeshed teeth 714a, 714b, such that movement of the first gear wheel 706a can cause movement of the second gear wheel 706b. The teeth 714a of the first gear wheel 706a can extend around a circumference thereof and face outwardly, e.g., extend radially outward. Similarly, the teeth 714b of the second gear wheel 706b can extend around a circumference thereof and face outwardly. The second floating wheel 724b can be operatively coupled to the second gear wheel 706b such that movement of the second gear wheel 706b can cause movement of the second floating wheel 724b. Thus, movement of the worm gear 710 can cause movement of the first and second gear wheels 706a, 706b and the first and second floating wheels 724a, 724b. The first and second rollers 708a, 710b and the worm gear 710 can together define a worm drive. The movement assembly 700 can thus include a single worm drive that includes a single worm gear 710 and a pair of opposed wheels 708a, 708b.

Similar to that discussed above regarding the first floating wheel 724a, the second floating wheel 724b can be configured to move translationally, as shown by arrow R10. The translational movement of the second floating wheel 724b can be relative to the second gear wheel 706b such that the second floating wheel 724b can "float" relative to the second gear wheel 706b. The translational movement of the second floating wheel 724b can be independent of the rotational movement of the second floating wheel 724b. A center shaft mount at a center point 726b of the second floating wheel 724b can be linearly movable to allow for the second floating wheel's translational movement. The center point 726b of the second floating wheel 724b is aligned with a center point 720b of the second gear wheel 706b in FIG. 12, but the center point 726b can become laterally offset therefrom as the second floating wheel 724b floats. The translational movement of the second floating wheel 724b can be substantially perpendicular to the longitudinal axis 704A of the shaft 704, which may facilitate gripping of the shaft 704 by the movement assembly 700 by allowing the second floating wheel 724b to move toward the shaft 704 and/or may help the movement assembly 700 accommodate surgical instruments of various diameters. A person skilled in the art will appreciate that the translational movement of the second floating wheel 724b may not be precisely perpendicular to the longitudinal axis 704A of the shaft 704 for any one or more reasons, e.g., manufacturing tolerances of the shaft 704, manufacturing tolerances of the second floating wheel 724b, accuracy of measurement devices, etc., but nevertheless be considered to be substantially perpendicular thereto.

The worm gear 710 can include a worm shaft 716 and have a thread 718 extending therearound. The worm gear 710 can be configured to rotate about a longitudinal axis A3 of the worm shaft 716, as shown by arrow R6. The worm gear's thread 718 can be operatively engaged with the teeth 714a of the first gear wheel 706a. Movement of the worm gear 710 can cause movement of the first gear wheel 706a due to the threaded engagement of the thread 718 and the teeth 714a. The movement of the first gear wheel 706a can cause movement of the first floating wheel 724a and movement of the second gear wheel 706b, which as mentioned above can each be operatively coupled to the first gear wheel 706a. The movement of the second gear wheel 706b can cause movement of the second floating wheel 724b operatively coupled thereto. Thus, rotation of the worm gear 710 about the longitudinal axis A3 of the worm shaft 716 can cause, as shown by arrow R7, the first gear wheel 706a to rotate about a center point 720a thereof and the first wheel 708a to rotate about a center point 726a thereof and can cause, as shown by arrow R8, the second gear wheel 706b to rotate about a center point 720b thereof and the second floating wheel 724b to rotate about a center point 726b thereof. In other words, torque $T_5$ of the worm gear 710, e.g., of the worm shaft 716, can be converted into torque $T_6$ of the first wheel 708a and torque $T_7$ of the second wheel 708b. The torques $T_5$, $T_6$, $T_7$ are shown in FIG. 12 for clockwise rotation of the worm gear 710 that causes counterclockwise rotation of the first wheel 708a and clockwise rotation of the second wheel 708b, but similar, opposite torques are produced for counterclockwise rotation of the worm gear 710 that causes clockwise rotation of the first wheel 708a and counterclockwise rotation of the second wheel 708b. The worm gear 710 can be configured to be driven by one or more of the motors of the robotic surgical system.

The worm gear 710 being configured to cause simultaneous rotation of the first and second wheel 708a, 708b, as discussed above, can allow facilitate selective proximal and distal translation of the instrument's shaft 704, as discussed further below.

The first floating wheel 724a of the first wheel 708a and the second floating wheel 724b of the second wheel 708b can be configured to engage the shaft 704 of the instrument 702 therebetween. The first and second floating wheels 724a, 724b can be spaced a distance apart from one another to define a gap 722 therebetween. The shaft 704 can be configured to be inserted into the gap 722 so as to be engaged between the first and second floating wheels 724a, 724b. The gap 722 has a variable width, e.g., the space between the first and second floating wheels 724a, 724b can be configured to change, due to the possible translational movements of the first and second floating wheels 724a, 724b. The gap 722 having a variable width can allow the movement assembly 700 to accommodate instrument shafts of various diameters, which may allow the robotic surgical system to be compatible with many different surgical instruments, may allow the robotic surgical system to be compatible with shafts having non-standard size diameters, may not limit the robotic surgical system to use with only one size of surgical instrument or to use with a limited number of predetermined sizes of surgical instruments. The width of the gap 722 can be configured to be automatically adjusted due to the dynamic translational movement of the first and second floating wheels 724a, 724b that can be in response to a size of the shaft 704 inserted therebetween. The gap 722 being automatically adjustable may allow the movement assembly 700 to be used with a variety of different surgical instruments and without the gap 722 having to be pre-adjusted by a user to the correct width for a selected surgical instrument.

The mounting of the first floating wheel 724a can be configured to provide a nominal, preloaded bias force $F_3$, e.g., a spring-loaded force, in a direction toward the second floating wheel 724b and hence toward the shaft 704 when engaged by the movement assembly 700. Similarly, the mounting of the second floating wheel 724b can be configured to provide a nominal, preloaded bias force $F_4$, e.g., a spring-loaded force, in a direction toward the first floating wheel 724a and hence toward the shaft 704 when engaged by the movement assembly 700. The preloaded bias forces $F_3$, $F_4$ can cooperate to help grip the shaft 704 positioned within the gap 722.

Similar to that discussed above with respect to the movement assembly 600 of FIG. 11, the rotation of the worm gear 710 can produce a reaction force $F_5$ in the first wheel 708a in addition to the torque force $T_6$ and can produce a reaction force $F_6$ in the second wheel 708b in addition to the torque force $T_7$. The preloaded bias force $F_3$ of the first floating wheel 724a can counteract the reaction force $F_5$ of the first wheel 708a, and the preloaded bias force $F_4$ of the second floating wheel 724b can counteract the reaction force $F_6$ of the second wheel 708b. The preloaded bias forces $F_3$, $F_4$ can thus help offset the reaction forces $F_5$, $F_6$ and consequently help prevent undesirable slippage of the shaft 704. A resultant force on the shaft 704 from the first and second wheels 708a, 708b can accordingly be a summation of the preloaded bias forces $F_3$, $F_4$ and the reaction forces $F_5$, $F_6$. The movement assembly 700 can thus be configured to make use of the "waste" forces reaction forces $F_3$, $F_4$ to help grip the shaft 704.

Surfaces of the first and second floating wheels 724a, 724b configured to engage the shaft 704 can each include a gripping feature configured to facilitate gripping of the shaft 704 by increasing a friction force therebetween. In at least some embodiments, the shaft 704 can include a gripping feature configured to facilitate gripping of the shaft 704 by the wheels 708a, 708b, e.g., the floating wheels 724a, 724b thereof.

When the shaft 704 is positioned within the gap 722 and is engaged by the first and second wheels 708a, 708b (e.g., by the first and second floating wheels 724a, 724b), the movement of the worm drive can cause translational movement of the shaft 704 (e.g., as shown by arrow R5) and hence cause translational movement of the instrument 702. The rotation of the worm drive (e.g., the rotation of the worm gear 716 and the rotation of the wheels 708a, 708b) can thus be translated into translational movement of the shaft 704, and hence of the instrument 702. The first and second wheels 708a, 708b can generally feed the shaft 704 proximally or distally, the direction depending on the directional rotation of the wheels 708a, 708b, similar to conveyor belt movement.

Figure 13:
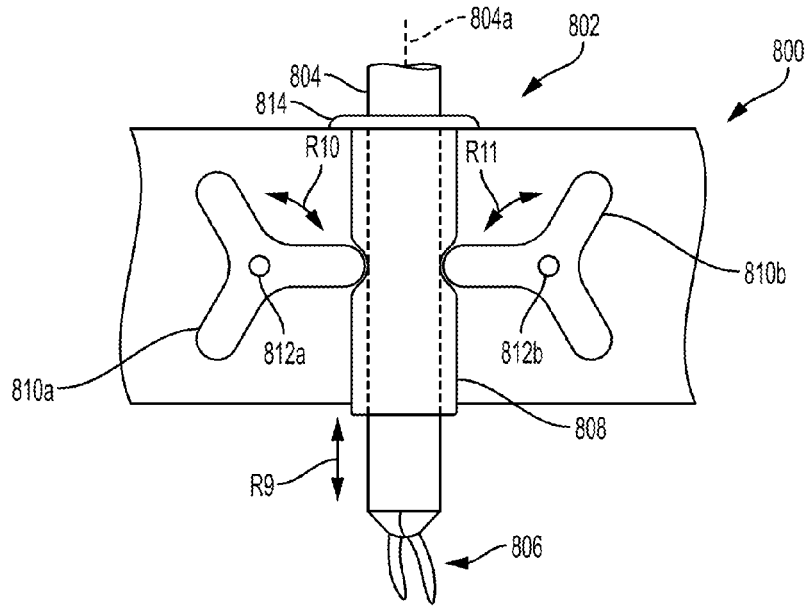
FIG. 13 is a side schematic view of yet another embodiment of a movement assembly of a robotic surgical system, the movement assembly being coupled to a shaft of a surgical instrument.

FIG. 13 illustrates one embodiment of a movement assembly 800 of a robotic surgical system configured to peristaltically drive a surgical instrument 802 coupled to the robotic surgical system to cause translational movement of the instrument 802. The surgical instrument 802 is partially illustrated in FIG. 13, with only a shaft 804 of the instrument 802 and an end effector 806 at a distal end of the shaft 804 illustrated in FIG. 13. The surgical instrument 802 can generally be configured and used similar to surgical instruments discussed herein and can have a handle at a proximal end of the shaft 804. The end effector 806 includes a pair of movable grasping jaws in this illustrated embodiment, but as mentioned above, the end effector 806 can have a variety of other configurations. The robotic surgical system can generally be configured and used similar to the robotic surgical system 200 of FIG. 3, e.g., can include at least one controller, at least one motor, and at least one movement mechanism. The movement assembly 800 can be operatively coupled to a movement mechanism, e.g., an electromechanical arm, of the robotic surgical system. In an exemplary embodiment, the movement assembly 800 can be fixed to the movement mechanism so as to be non-removable therefrom.

The controller of the robotic surgical system can be configured to receive an input from a user (not shown) requesting movement, relative to a patient (not shown), of the instrument 802. The user can provide the input using a user input device (not shown), as discussed herein. The controller can be configured to cause the motor (not shown) of the robotic surgical system to drive movement of the movement mechanism and/or the movement assembly 800, thereby causing movement of the surgical instrument 802 coupled thereto. The movement mechanism can be configured to move, as discussed above, to cause various movements of the surgical instrument 802, such as angular adjustments of the instrument 802 relative to the patient, actuation of the end effector 806 (e.g., opening/closing of the jaws), etc. The movement assembly 800 can be configured to move, as discussed further below, to cause translational movement of the surgical instrument 802 in opposed proximal and distal directions along a longitudinal axis 804A of the instrument's shaft 804, as indicated by arrow R9.

As in this illustrated embodiment, the movement assembly 800 can include a sleeve 808 and a peristaltic pump that includes a pair of opposed rotors 810*a*, 810*b*. The rotors 810*a*, 810*b* can have a variety of configurations. The rotors 810*a*, 810*b* can be operatively coupled to the at least one motor of the robotic surgical system, which can be configured to drive movement (e.g., rotation) of the rotors 810*a*, 810*b*. In this way, user input to the motor(s) via the input device can cause movement of the rotors 810*a*, 810*b* and, hence, movement of the instrument 802, as discussed further below.

The rotors 810*a*, 810*b* can each have a same number of lobes (also referred to herein as "cams") extending radially outward from a central base portion thereof including a center point 812*a*, 812*b* which the lobes rotate. By the rotors 810*a*, 810*b* having a same number of cams as one another, the cams of the respective rotors 810*a*, 810*b* can cooperatively act on the sleeve 808 at a same time as one another to maximize efficient movement of the instrument 802 within the sleeve 808. The rotors 810*a*, 810*b* each have three cams in this illustrated embodiment but can, in other embodiments, have another number of cams (e.g., two, four, five, etc.).

The rotors 810*a*, 810*b* can be configured to simultaneously rotate in opposite directions from one another, e.g., the first rotor 810*a* rotating clockwise and the second rotor 810*b* rotating counterclockwise. Arrows R10, R11 show the possible rotational movement of the rotors 810*a*, 810*b*, respectively. The first rotor 810*a* rotating counterclockwise while the second rotor 810*b* rotates clockwise can cause movement of the shaft 804 of the instrument 802 in a proximal direction along the shaft's longitudinal axis 804A, and the first rotor 810*a* rotating clockwise while the second rotor 810*b* rotates counterclockwise can cause movement of the shaft 804 of the instrument 802 in a distal direction along the shaft's longitudinal axis 804A. In other words, the cooperating movement of the rotors 810*a*, 810*b* in opposite directions from one another can selectively move the shaft 804 proximally or distally. A speed at which the rotors 810*a*, 810*b* rotate can define how quickly the shaft 804 translates, e.g., a faster speed of the rotors 810*a*, 810*b* corresponds to faster translation of the shaft 804. The shaft 804 can thus be moved at a speed desired by a user, which may allow the user to more finely control movement of the shaft 804 and ensure that the instrument 802 is desirably positioned without interfering with any other objects, e.g., a patient, other instruments, etc.

The sleeve 808 can have a variety of configurations. The sleeve 808 can be configured to deform, such as by being pliable or elastomeric, in response to being pinched between the rotors' lobes. The deformability of the sleeve 808 can allow the sleeve to expand and contract radially so as to accommodate different size shaft 804 diameters therein, e.g., to expand and contract radially in response to the shaft 804 being inserted therein so as to dynamically adjust to the shaft's diameter. Alternatively, the sleeve 808 can be configured to maintain a substantially constant diameter, e.g., not expand and contract radially in response to the shaft 804 being inserted therein, while still having sufficient deformability to deform in response to pressure applied thereto from the rotors 810*a*, 810*b*.

In addition to or in alternative to the sleeve 808 being deformable to accommodate different size shaft 804 diameters therein, the rotors 810*a*, 810*b* can be configured to move laterally inward and outward, e.g., toward and away from the sleeve 808, to accommodate instrument shafts of various diameters. This movement of the rotors 810*a*, 810*b* can be similar to that discussed above regarding the movement of the first and second wheels 608*a*, 608*b* to adjust the width of the gap 622. Thus, the rotors 810*a*, 810*b* can be configured to be manually adjusted, such as by moving the first and second rotors 810*a*, 810*b* to be separated a desired distance from one another and locking the first and second rotors 810*a*, 810*b* in position using a locking mechanism, or the rotors 810*a*, 810*b* can be configured to be automatically adjusted, such as by the first and second wheels 810*a*, 810*b* being spring-mounted and biased toward each other.

In at least some embodiments, the sleeve 808 can be configured to be removable and replaceable from the movement assembly 800, such as by being selectively attached and removed from an anchor 814. This removability and replaceability may facilitate cleaning of the sleeve 808 during and/or after a surgical procedure, may facilitate disposability of the sleeve 808 after use, and/or may allow different sizes sleeves to be selectively attached to the movement assembly 800. For example, a sleeve 808 having a diameter corresponding to a diameter of the shaft 804 can be attached to the movement assembly 800 and replaced with other sleeve(s) during performance of the surgical procedure and/or for performance of another surgical procedure. In at least some embodiments, each of a plurality of sleeves configured to be removably and replaceably attached to the movement assembly 800 can have a same outer diameter to facilitate engagement of the attached sleeve with the rotors 810*a*, 810*b* and can have a different inner diameter to facilitate insertion therein of surgical instruments of different diameters. For example, a wall thickness of each of the sleeves can be different from one another such that each of the sleeves has a different inner diameter.

In at least some embodiments, the sleeve 808 can be an integral part of a surgical drape or other textile used during a surgical procedure, which may facilitate disposability of the sleeve 808.

The rotors 810*a*, 810*b* can be configured to act on the sleeve 808 during rotation of the rotors 810*a*, 810*b*. In other words, the rotors 810*a*, 810*b*, e.g., the lobes thereof, can be configured to sequentially and operatively engage the sleeve 808 during rotation of the rotors 810*a*, 810*b*. The action of the rotors 810*a*, 810*b* on the sleeve 808, e.g., the engagement of the rotors' lobes on the sleeve 808, can cause the sleeve 808 to deform and consequently apply friction to the shaft 804 and cause the shaft 804 disposed within the sleeve to translate along its longitudinal axis 804A. The sleeve 808 can be fixed in position in the movement assembly 800, such as by being fixed to the movement mechanism and/or other part of the robotic surgical system with the anchor 814 (e.g., any one or more of a washer, an adhesive, a press fit cap, etc.), such that the shaft 804 can be moved within the sleeve 808 by the rotors' rotation and engagement of the sleeve 808. The rotors' lobes can be configured to push the shaft 804 disposed within the sleeve 808 proximally (with the first rotor 810*a* rotating counterclockwise and the second rotor 810b rotating clockwise) or distally (with the first rotor 810a rotating clockwise and the second rotor 810b rotating counterclockwise). The sleeve 808 can thus act as a barrier between the shaft 804 and the rotors 810a, 810b, which may help protect the shaft 804. The rotors 810a, 801b directly engaging the sleeve 808 instead of directly engaging the shaft 804 disposed within the sleeve 808 may provide a more frictional surface for the rotors 810a, 810b to engage, which may more efficiently translate the rotational motion of the rotors 810a, 810b to the translational motion of the shaft 804. Surgical instrument shafts such as the shaft 804 are typically metallic, while the sleeve 808 can made from a plastic or other polymer that has a higher coefficient of friction than metal.

Figure 14:
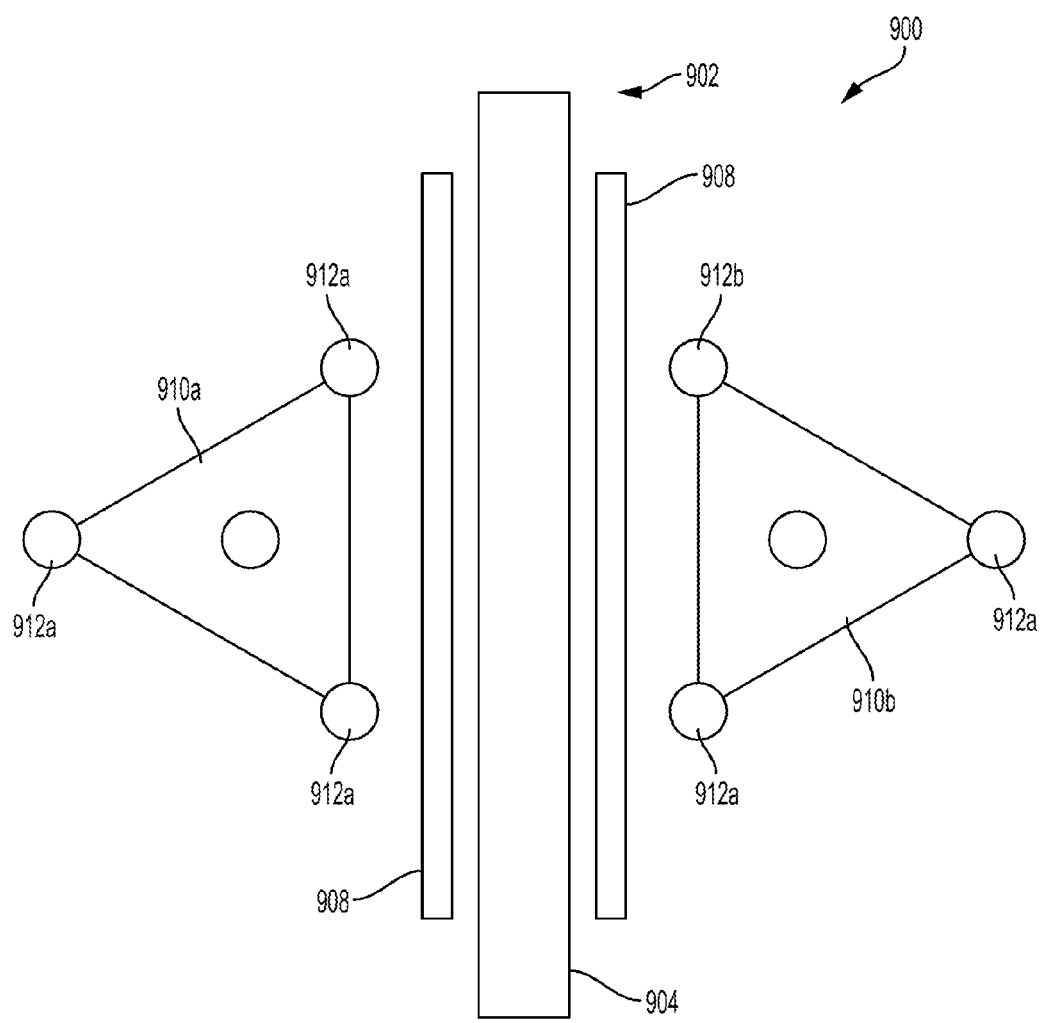
FIG. 14 is a side schematic view of another embodiment of a movement assembly of a robotic surgical system, the movement assembly being coupled to a shaft of a surgical instrument.

FIG. 14 illustrates another embodiment of a movement assembly 900 of a robotic surgical system configured to peristaltically drive a surgical instrument 902 coupled to the robotic surgical system to cause translational movement of the instrument 902. The surgical instrument 902 is partially illustrated in FIG. 14, with only a shaft 904 of the instrument 902 illustrated in FIG. 14. The surgical instrument 902 can generally be configured and used similar to surgical instruments discussed herein and can have a handle at a proximal end of the shaft 904 and an end effector at a distal end of the shaft 904. The robotic surgical system can generally be configured and used similar to the robotic surgical system 200 of FIG. 3, e.g., can include at least one controller, at least one motor, and at least one movement mechanism. The movement assembly 900 can be operatively coupled to a movement mechanism, e.g., an electromechanical arm, of the robotic surgical system. In an exemplary embodiment, the movement assembly 900 can be fixed to the movement mechanism so as to be non-removable therefrom.

The movement assembly 900 of FIG. 14 can be generally configured and used similar to the movement assembly 800 of FIG. 13 and can include a sleeve 908 and a peristaltic pump that includes a pair of opposed rotors 910a, 910b. The rotors 910a, 910b each include three lobes configured to sequentially and correspondingly engage the sleeve 908 to move the instrument shaft 904 disposed within the sleeve 908, similar to that discussed above regarding the movement assembly 800.

The lobes of the rotors 910a, 910b in this illustrated embodiment include engagement members 912a, 912b at outward-most ends thereof. The engagement members 912a, 912b can be configured to facilitate engagement of the rotors 910a, 910b with the sleeve 908 and, consequently, pinching of the sleeve 908 and the shaft 904 disposed within the sleeve 908. The engagement members 912a, 912b can have a variety of configurations. As in this illustrated embodiment, the engagement members 912a, 912b can have rounded edges, such as by being in the form of spheres or eggs at the outward-most ends, which may facilitate pinching of the sleeve 908 and the shaft 904 therein without puncturing, cutting, or otherwise damaging the sleeve 908.

Figure 15:
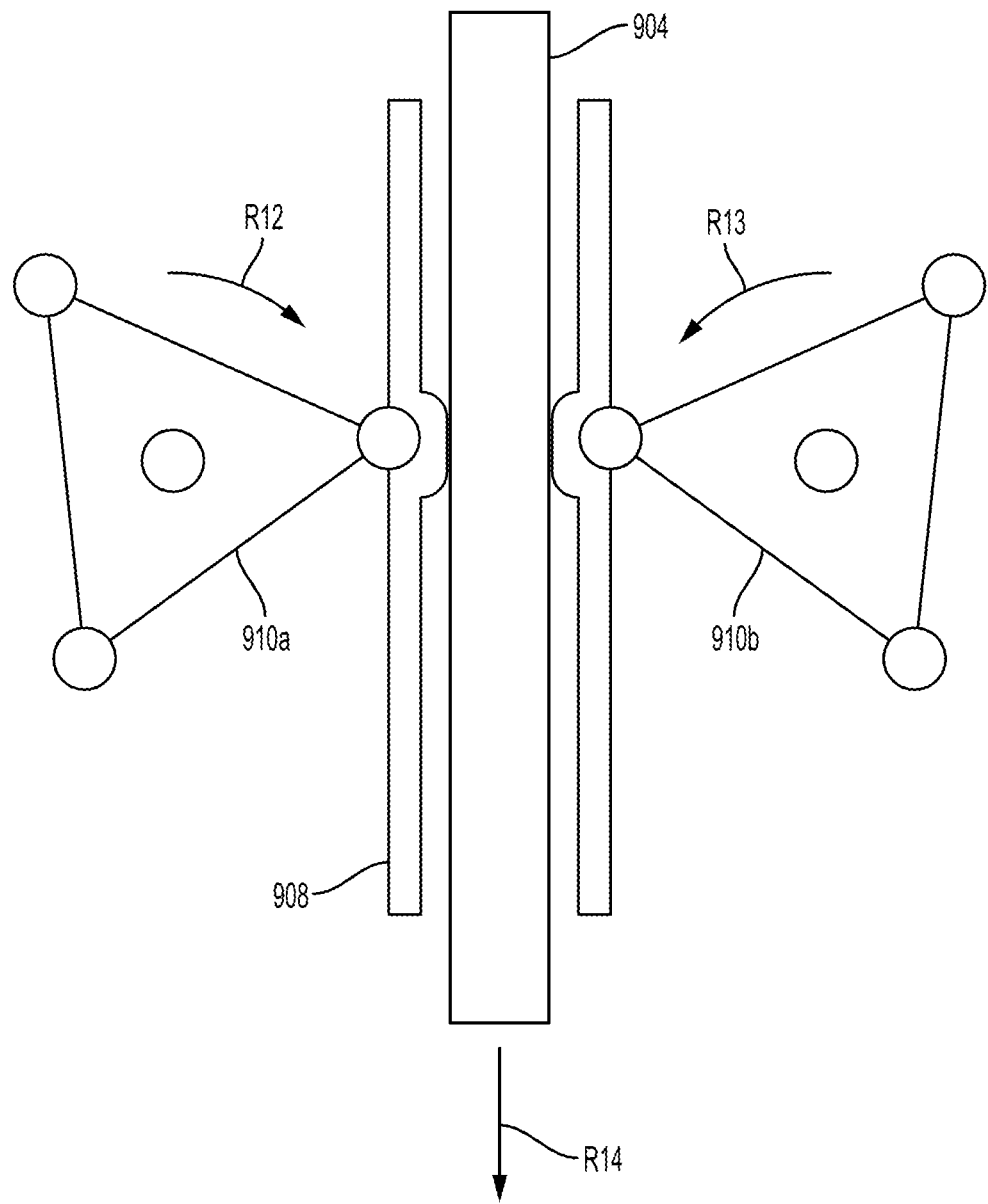
FIG. 15 is a side schematic view of the movement assembly of FIG. 14 with rotors of the movement assembly in a position that is rotated from a position of the rotors in FIG. 14 and with the shaft advanced distally from its position in FIG. 14.
Figure 16:
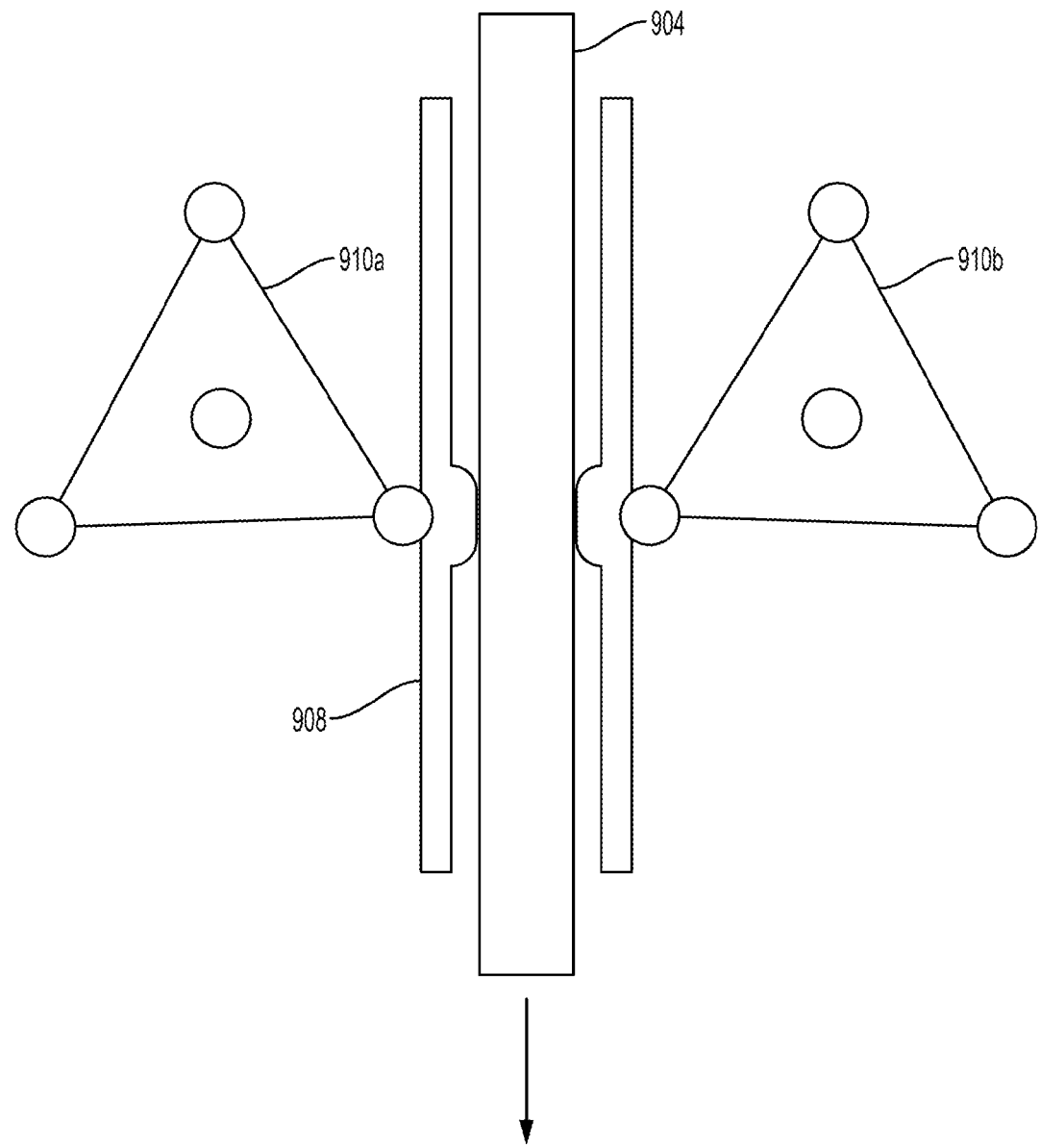
FIG. 16 is a side schematic view of the movement assembly of FIG. 15 with rotors of the movement assembly in a position that is rotated from the position of the rotors in FIG. 15 and with the shaft advanced distally from its position in FIG. 15.

FIG. 14 shows the shaft 904 disposed within the sleeve 908 without the rotors 910a, 910b engaging the sleeve 908, e.g., without any of the rotors' lobes touching the sleeve 908. FIG. 15 shows the rotors 910a, 910b rotated from their position in FIG. 14, with the first rotor 910a having been rotated clockwise as shown by arrow R12 and the second rotors 910b having been rotated counterclockwise as shown by arrow R13, such that one lobe 912a, 912b of each of the rotors 910a, 910b has engaged the sleeve 908. The engagement of the rotors 910a, 910b with the sleeve 908 can pinch and cause deformation of the sleeve 908, as shown in FIG. 15, which may facilitate gripping and movement of the shaft 904 within the sleeve 908. The direction of rotation of the rotors 910a, 910b in FIG. 15 has caused the shaft 904 to move in a distal direction, as shown by arrow R14. The rotors 910a, 901b can, however, rotate in opposite directions so as to cause proximal movement of the shaft 904, as discussed herein. FIG. 16 shows the rotors 910a, 910b rotated from their position in FIG. 15, with the first rotor 910a having been further rotated clockwise and the second rotors 910b having been rotated further counterclockwise, such that the one lobe 912a, 912b of each of the rotors 910a, 910b engaging the sleeve 908 has moved distally to cause further distal movement of the shaft 904.

Figure 17:
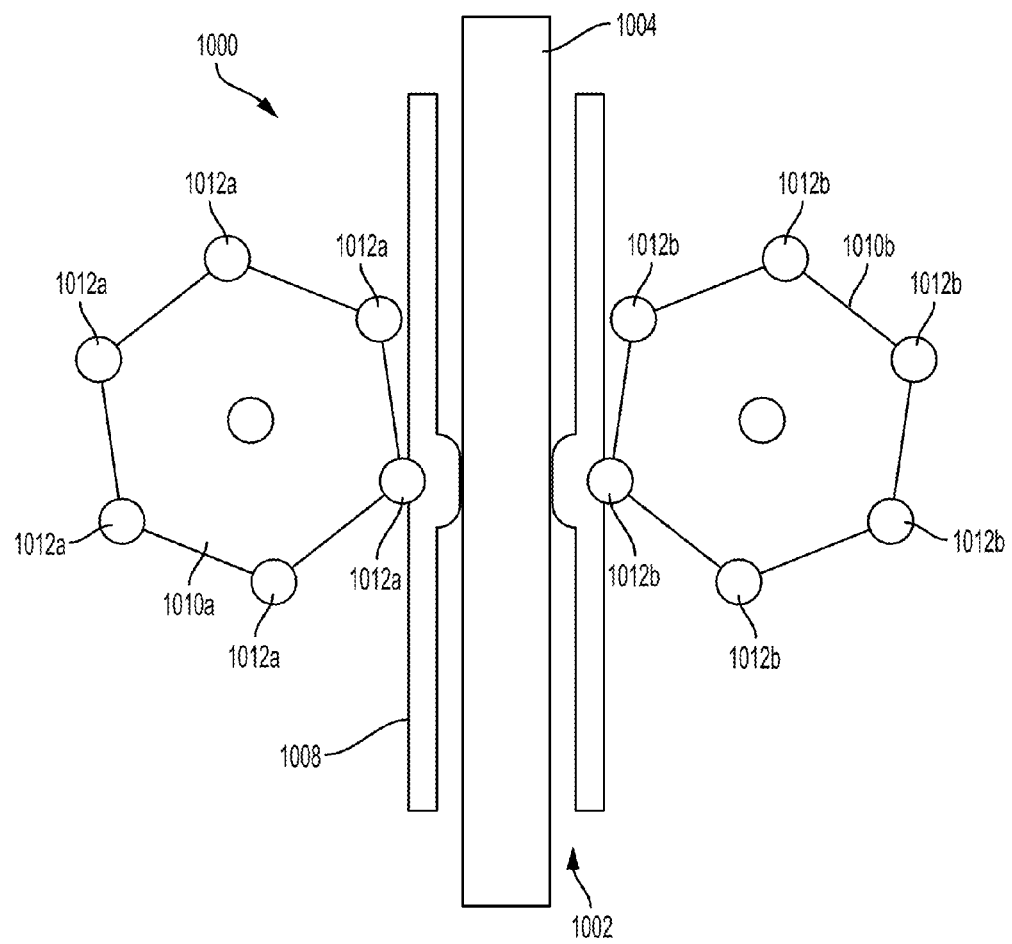
FIG. 17 is a side schematic view of still another embodiment of a movement assembly of a robotic surgical system, the movement assembly being coupled to a shaft of a surgical instrument.

FIG. 17 illustrates another embodiment of a movement assembly 1000 of a robotic surgical system configured to peristaltically drive a surgical instrument 1002 coupled to the robotic surgical system to cause translational movement of the instrument 1002. The surgical instrument 1002 is partially illustrated in FIG. 17, with only a shaft 1004 of the instrument 1002 illustrated in FIG. 17. The surgical instrument 1002 can generally be configured and used similar to surgical instruments discussed herein and can have a handle at a proximal end of the shaft 1004 and an end effector at a distal end of the shaft 1004. The robotic surgical system can generally be configured and used similar to the robotic surgical system 200 of FIG. 3, e.g., can include at least one controller, at least one motor, and at least one movement mechanism. The movement assembly 1000 can be operatively coupled to a movement mechanism, e.g., an electromechanical arm, of the robotic surgical system. In an exemplary embodiment, the movement assembly 1000 can be fixed to the movement mechanism so as to be non-removable therefrom.

The movement assembly 1000 of FIG. 17 can be generally configured and used similar to the movement assembly 800 of FIG. 13 and can include a sleeve 1008 and a peristaltic pump that includes a pair of opposed rotors 1010a, 1010b. The rotors 1010a, 1010b each include six lobes configured to sequentially and correspondingly engage the sleeve 1008 to move the instrument shaft 1004 disposed within the sleeve 1008, similar to that discussed above regarding the movement assembly 800. The rotors' lobes each include an engagement member 1012a, 1012b at outermost ends thereof. The engagement members 1012a, 1012b can be configured and used similar to the engagement members 912a, 912b of FIG. 14 discussed above.

Figure 18:
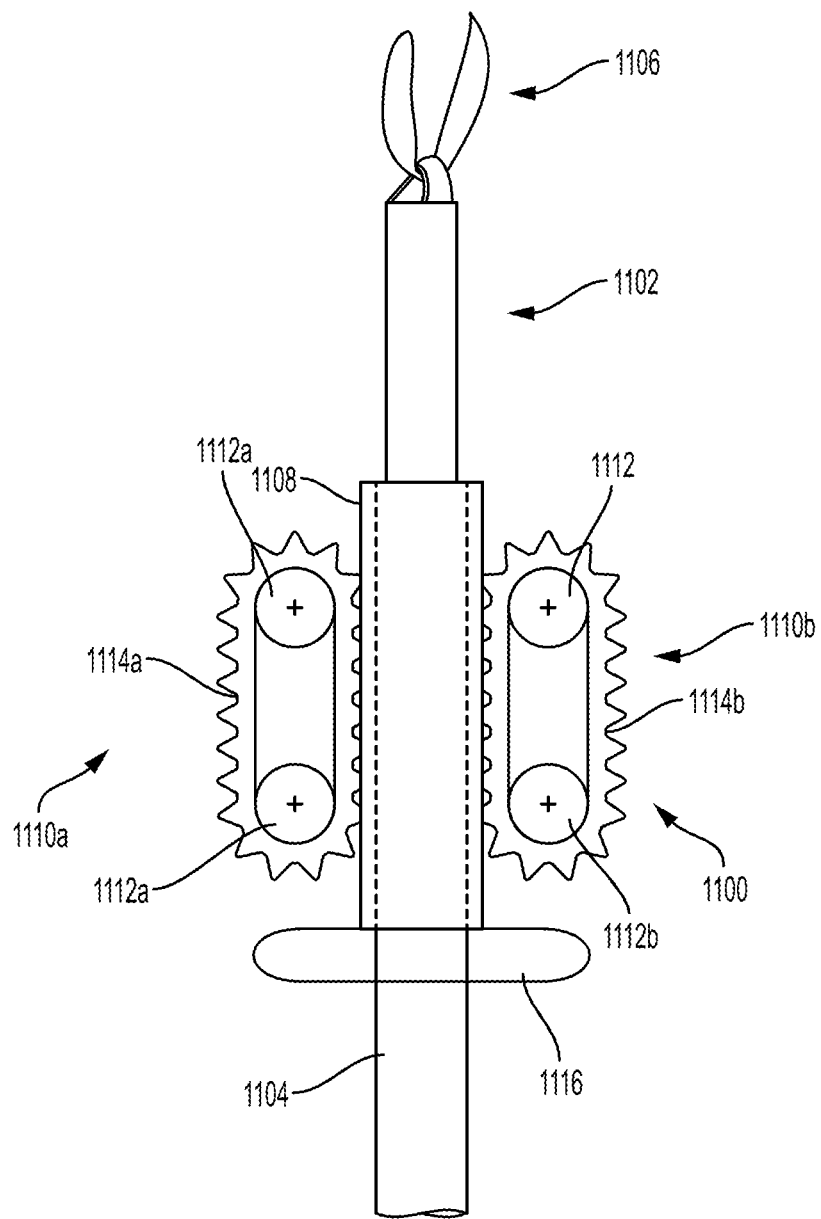
FIG. 18 is a side schematic view of another embodiment of a movement assembly of a robotic surgical system, the movement assembly being coupled to a shaft of a surgical instrument.

FIG. 18 illustrates another embodiment of a movement assembly 1100 of a robotic surgical system configured to peristaltically drive a surgical instrument 1102 coupled to the robotic surgical system to cause translational movement of the instrument 1102. The surgical instrument 1102 is partially illustrated in FIG. 18, with only a shaft 1104 and an end effector 1106 of the instrument 1102 illustrated in FIG. 18. The surgical instrument 1102 can generally be configured and used similar to surgical instruments discussed herein and can have a handle at a proximal end of the shaft 1104. The end effector 1106 includes a pair of movable grasping jaws in this illustrated embodiment, but as mentioned above, the end effector 1106 can have a variety of other configurations. The robotic surgical system can generally be configured and used similar to the robotic surgical system 200 of FIG. 3, e.g., can include at least one controller, at least one motor, and at least one movement mechanism. The movement assembly 1100 can be operatively coupled to a movement mechanism, e.g., an electromechanical arm, of the robotic surgical system. In an exemplary embodiment, the movement assembly 1100 can be fixed to the movement mechanism so as to be non-removable therefrom.

The movement assembly 1100 of FIG. 17 can be generally configured and used similar to the movement assembly 800 of FIG. 13 and can include a sleeve 1108 and a peristaltic pump that includes a pair of opposed rotors 1110a, 1110b. As in this illustrated embodiment, each of the rotors 1110a, 1110b can include a pair of rollers 1112a, 1112b and a belt 1114a, 1114b configured to be driven by the pair of rollers 112a, 1112b associated therewith. At least one of each pair of rollers 1112a, 1112b can be operatively coupled to the at least one motor of the robotic surgical system, which can be configured to drive movement (e.g., rotation) of the rollers 1112a, 1112b. In this way, user input to the motor(s) via the input device can cause movement of the rotors 1110a, 1110b and, hence, movement of the instrument 1102, as discussed herein. Each of the belts 1114a, 1114b can have a plurality of lobes extending radially outward therefrom that can be configured to engage the sleeve 1108 similar to the rotor lobes discussed above with respect to FIGS. 13-17. The belts 1114a, 1114b can each be configured to constantly engage the sleeve 1108 with a plurality of lobes, which may help prevent unintended slippage of the shaft 1104 regardless of whether the belts 1114a, 1114b are rotating or not. FIG. 17 also shows the sleeve 1108 mounted in position with an anchor 1116, which can be generally configured and used similar to the anchor 814 discussed above with respect to FIG. 13.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, components of the invention described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

Typically, the device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. Pub. No. 2009/0202387 filed Feb. 8, 2008 and entitled "System And Method Of Sterilizing An Implantable Medical Device." It is preferred that device, if implanted, is hermetically sealed. This can be done by any number of ways known to those skilled in the art.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical system, comprising:
   an electromechanical arm configured for movement in multiple axes;
   an electromechanical tool having an instrument shaft and an end effector formed thereon, the electromechanical tool being configured to be mounted on the electromechanical arm, and the electromechanical tool being configured to move relative to the electromechanical arm;
   a second electromechanical tool having a second instrument shaft and a second end effector formed thereon; and
   a tool controller operatively coupled to the electromechanical arm and the electromechanical tool, the tool controller including opposed rollers that receive the electromechanical tool therebetween, the rollers being configured for cooperative rotational movement effective to translate the electromechanical tool, and the rollers being configured for linear movement toward and away from the electromechanical tool and thereby accommodate a diameter of the electromechanical tool while providing a compressive force on the electromechanical tool;
   wherein the second electromechanical tool is configured to be mounted on the electromechanical arm, the second electromechanical tool is configured to move relative to the electromechanical arm, a diameter of the second electromechanical tool is different than the diameter of the electromechanical tool, the rollers are configured for linear movement toward and away from the second electromechanical tool and thereby accommodate the diameter of the second electromechanical tool while providing a second compressive force on the second electromechanical tool, and the second compressive force is different than the compressive force.

2. The system of claim 1, wherein the tool controller includes opposed worm gears, each of the worm gears being operatively coupled to one of the opposed rollers.

3. The system of claim 2, wherein the worm gears are configured for cooperative rotational movement effective to cause the rotational movement of the rollers.

4. The system of claim 1, wherein the tool controller includes a single worm gear operatively coupled to one of the opposed rollers and configured to rotate to cause rotation of both of the opposed rollers.

5. The system of claim 1, wherein the tool controller includes opposed gears each having one of the rollers operatively coupled thereto, the gears being configured for cooperative rotational movement effective to cause the rotational movement of the rollers.

6. The system of claim 5, wherein the tool controller includes opposed worm gears, each of the worm gears has teeth, and each of the opposed gears has teeth operatively engaged with the teeth of one of the worm gears.

7. The system of claim 6, wherein the worm gears are configured for cooperative rotational movement effective to cause the rotational movement of the opposed gears.

8. The system of claim 1, wherein the compressive force is a variable force dependent on the diameter of the electromechanical tool.

9. The system of claim 1, further comprising a processor configured to receive a user input and configured to cause the cooperative rotational movement of the rollers in response to the received user input.

10. The system of claim 2, wherein the opposed rollers are configured to simultaneously rotate in opposite directions and thereby cause translation of the electromechanical tool received by the opposed rollers, and the opposed worm gears are each configured to simultaneously rotate to cause the opposed rollers to simultaneously rotate in the opposite directions.

11. A surgical system, comprising:
an electromechanical arm configured for movement in multiple axes;
a pliable sleeve coupled to the electromechanical arm;
an electromechanical tool having an instrument shaft and an end effector formed thereon, the electromechanical tool being configured to be mounted within the pliable sleeve; and
a tool driver having opposed rotors having the pliable sleeve positioned therebetween, the opposed rotors each having a plurality of lobes and each being capable of cooperative rotational movement such that the lobes sequentially engage the pliable sleeve to generate friction that translates the electromechanical tool within the pliable sleeve.

12. The system of claim 11, wherein the opposed rotors each include a central base having the plurality of lobes extending radially outward therefrom.

13. The system of claim 11, wherein the opposed rotors each include a belt having the plurality of lobes and a roller configured to rotate to drive the belt.

14. The system of claim 11, wherein the translation of the electromechanical tool within the pliable sleeve includes longitudinal translation of the electromechanical tool along a longitudinal axis of the instrument shaft of the electromechanical tool.

15. The system of claim 11, further comprising a processor configured to receive a user input and configured to cause the cooperative rotational movement of the lobes in response to the received user input.

16. A surgical system, comprising:
an electromechanical arm configured to removably couple to a surgical instrument, the electromechanical arm being configured to move so as to move the surgical instrument removably coupled thereto relative to a patient on which a surgical procedure is being performed;
an elastomeric sleeve configured to receive the surgical instrument therein; and
a peristaltic pump operatively coupled to the electromechanical arm, the peristaltic pump including opposed rotors each being configured to rotate to apply a cooperative force to the sleeve and thereby cause the surgical instrument received in the sleeve to longitudinally translate relative to the sleeve.

17. The system of claim 16, wherein the opposed rotors each include a central base having a plurality of lobes extending radially outward therefrom.

18. The system of claim 16, wherein the opposed rotors each include a belt having a plurality of lobes and a roller configured to rotate to drive the belt.

19. The system of claim 16, further comprising a processor configured to receive a user input and configured to cause the rotation of the opposed rotors in response to the received user input.

* * * * *